(12) United States Patent
Marshall et al.

(10) Patent No.: US 10,946,190 B2
(45) Date of Patent: Mar. 16, 2021

(54) EPICARDIAL DEFIBRILATION LEAD WITH SIDE HELIX FIXATION AND PLACEMENT THEREOF

(71) Applicant: Medtronic, Inc., Minneapolis, MN (US)

(72) Inventors: Mark T. Marshall, Forest Lake, MN (US); Andrea J. Asleson, Maple Grove, MN (US); Jean Rutten, Gulpen (NL)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 16/227,309

(22) Filed: Dec. 20, 2018

(65) Prior Publication Data
US 2019/0117960 A1 Apr. 25, 2019

Related U.S. Application Data

(62) Division of application No. 15/234,481, filed on Aug. 11, 2016, now Pat. No. 10,195,421.
(Continued)

(51) Int. Cl.
*A61N 1/05* (2006.01)
*A61N 1/39* (2006.01)
*A61N 1/365* (2006.01)

(52) U.S. Cl.
CPC ......... *A61N 1/059* (2013.01); *A61N 1/36514* (2013.01); *A61N 1/3956* (2013.01);
(Continued)

(58) Field of Classification Search
CPC .. A61N 1/059; A61N 1/36514; A61N 1/3956; A61N 1/3987; A61N 1/0592; A61N 1/365; A61N 1/3968
See application file for complete search history.

(56) References Cited

U.S. PATENT DOCUMENTS 5,443,492 A 8/1995 Stokes et al.
5,871,532 A 2/1999 Schroeppel
(Continued)

FOREIGN PATENT DOCUMENTS

EP 2394695 A1 12/2011

OTHER PUBLICATIONS

Haydin et al. "Subxiphoid Approach to Epicardial Implantation of Implantable Cardioverter Defibrillators in Children", PACE, vol. 00, 2013, 5 pages.
(Continued)

*Primary Examiner* — Paula J Stice

(57) ABSTRACT

A method and system for employing a medical device is disclosed. The medical device includes a housing, a processor disposed within the housing, a connector module, and a medical electrical epicardial lead connected to the processor through the connector module. The epicardial lead is used to sense a cardiac signal from tissue of a patient. The lead comprises an insulative lead body that includes a proximal end and a distal end, at least one conductor disposed in the lead body, and a side helical fixation member, disposed a distance from the distal end, the side helical fixation member. The side helical fixation member comprises a set of windings configured to wrap around the lead body circumference. The side helical fixation member includes a distal tip comprising a sharpened elongated flat free end that is perpendicular to the lead body and angled toward an inside of the set of windings.

18 Claims, 20 Drawing Sheets

Related U.S. Application Data

(60) Provisional application No. 62/204,343, filed on Aug. 12, 2015, provisional application No. 62/211,331, filed on Aug. 28, 2015.

(52) U.S. Cl.
CPC .......... *A61N 1/3987* (2013.01); *A61N 1/0592* (2013.01); *A61N 1/365* (2013.01); *A61N 1/3968* (2013.01)

(56) References Cited

U.S. PATENT DOCUMENTS

| | | |
|---|---|---|
| 6,418,346 B1 | 7/2002 | Nelson et al. |
| 6,442,433 B1 | 8/2002 | Linberg |
| 6,480,745 B2 | 11/2002 | Nelson et al. |
| 6,493,591 B1 | 12/2002 | Stokes |
| 6,556,874 B2 | 4/2003 | Audoglio |
| 6,599,250 B2 | 7/2003 | Webb et al. |
| 6,622,045 B2 | 9/2003 | Snell et al. |
| 7,162,309 B2 | 1/2007 | Laske et al. |
| 7,212,871 B1 | 5/2007 | Morgan |
| 7,251,532 B2 | 7/2007 | Hess et al. |
| 7,313,445 B2 | 12/2007 | McVenes et al. |
| 7,529,584 B2 | 5/2009 | Laske et al. |
| 7,532,939 B2 | 5/2009 | Sommer et al. |
| 7,601,033 B2 | 10/2009 | Ries et al. |
| 7,610,104 B2 | 10/2009 | Kaplan et al. |
| 7,654,843 B2 | 2/2010 | Olson et al. |
| 7,783,365 B2 | 8/2010 | Ebert et al. |
| 7,860,580 B2 | 12/2010 | Falk et al. |
| 7,920,928 B1 | 4/2011 | Yang et al. |
| 8,005,549 B2 | 8/2011 | Boser et al. |
| 8,346,373 B2 | 1/2013 | Thompson-Nauman et al. |
| 8,670,824 B2 | 3/2014 | Anderson et al. |
| 8,755,909 B2 | 6/2014 | Sommer et al. |
| 8,825,180 B2 | 9/2014 | Bauer et al. |
| 9,155,868 B2 | 10/2015 | Drake et al. |
| 2007/0250144 A1 | 10/2007 | Falk et al. |
| 2013/0325094 A1* | 12/2013 | Sommer ............ A61N 1/0573 607/127 |
| 2014/0005762 A1 | 1/2014 | Wu et al. |
| 2015/0320996 A1 | 11/2015 | Eggen et al. |
| 2016/0143758 A1 | 5/2016 | Gardeski et al. |
| 2017/0043155 A1 | 2/2017 | Marshall et al. |

OTHER PUBLICATIONS (PCT/US2016/046679) PCT Notification of Transmittal of the International Search Report and the Written Opinion of the International Searching Authority, dated Nov. 4, 2016, 9 pages.

* cited by examiner

EPICARDIAL DEFIBRILATION LEAD WITH SIDE HELIX FIXATION AND PLACEMENT THEREOF

CROSS-REFERENCE TO RELATED APPLICATIONS

This application claims the benefit of U.S. Provisional Application No. 62/204,343, filed on Aug. 12, 2015, and U.S. Provisional Application No. 62/211,331 filed on Aug. 28, 2016. The disclosures of the above applications are incorporated herein by reference in their entirety. This application is a divisional of U.S. application Ser. No. 15/234,481, filed on Aug. 11, 2016 by Marshall, et al., now issued as U.S. Pat. No. 10,185,421.

TECHNICAL FIELD

The present disclosure relates generally to implantable medical leads, and, more particularly, to techniques for placement of medical electrical leads.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

IMDs detect and deliver therapy for a variety of medical conditions in patients. IMDs include implantable pulse generators (IPGs) or implantable cardioverter-defibrillators (ICDs) that deliver electrical stimuli to tissue of a patient. ICDs typically comprise, inter alia, a control module, a capacitor, and a battery that are housed in a hermetically sealed container with a lead extending therefrom. It is generally known that the hermetically sealed container can be implanted in a selected portion of the anatomical structure, such as in a chest or abdominal wall, and the lead tip portion can be positioned at the selected position near or in the muscle group. When therapy is required by a patient, the control module signals the battery to charge the capacitor, which in turn discharges electrical stimuli to tissue of a patient via electrodes disposed on the lead, e.g., typically near the distal end of the lead. Typically, a medical electrical lead includes a flexible elongated body with one or more insulated elongated conductors. Each conductor electrically couples a sensing and/or a stimulation electrode of the lead to the control module through a connector module.

In order to deliver stimulation or to perform sensing functions, it is desirable for the distal end of a medical electrical lead to substantially remain in its position, as originally implanted by a physician. Leads are typically implanted endocardially such that the lead is transvenously introduced with the distal end of the lead positioned in one of the chambers. In contrast to endocardial leads, epicardial leads are introduced outside of the cardiovascular system to bring the distal end in contact with the epicardial or myocardial tissue. Numerous scenarios exist in which epicardial leads are preferred over endocardial leads such as when patients possess inadequate vascular access. Children, for example, may require an epicaridal lead instead of an endocardial lead. Additionally, some congenital heart disease patients require the use of an epicardial lead. Moreover, patients in which placement of a lead through the coronary sinus for delivery of cardiac resynchronization therapy that has failed may benefit by placement of an epicardial lead in a more optimal pacing site location such as the outer surface of the heart.

Epicardial lead implantation requires surgical access to allow sufficient room to position and fixate the pacing lead by either sutures or a right angle helical screw component. Surgical access is more traumatic and requires longer recovery time as compared to percutaneous implant methods. One such percutaneous implant method has been described in Subxiphoid Approach to Epicardial Implantation of Implantable Cardioverter Defibrillators in Children, Sertac Haydin, M.D. et al. PACE, Vol. 00 (2013). In the Haydin article, a transvenous ICD lead was introduced through a subxiphoid percutaneous approach such that the extendable-retractable helix was screwed into non-cardiac tissue for fixation without pacing or sensing capability through the ICD lead.

Another epicardial implantation method is described in U.S. Pat. No. 5,443,492 to Stokes et al. which involves an epicardial lead in which an active fixation mechanism secures the lead in place while allowing a distal electrode on the lead to mechanically "float" with respect to the body tissue. The active fixation mechanism comprises a curved hook disposed at the distal end of the lead. The curved hook defines a helix around at least a portion of the lead's circumference. A hollow introducer needle is slidably disposed on the lead. The hollow needle provided with a longitudinal slit in a distal section of is length, such that the distal section of the needle can be advanced over the distal end of the lead, past the fixation hook, which is received in the longitudinal slit.

The Stokes et al. lead is unable to be fixated solely in the epicardial tissue since the lead penetrates beyond the epicardium and resides mid-myocardial for stimulation. This is due to the hollow needle that interlocks with the side hook. The needle is jabbed into the surface driving the tip (i.e. electrode) of the lead deeply into the heart myocardium. The needle is then twisted or torqued (i.e. bayonet style) into the tissue. Thereafter, the needle is withdrawn leaving the lead tip disposed intramyocardial.

Numerous other lead configurations have employed side helical fixation members such as U.S. Pat. No. 8,755,909 B2 to Sommer et al. incorporated by reference in its entirety. One type of left lead adapted for placement in the coronary vasculature is that disclosed in U.S. Pat. No. 7,860,580, issued to Sommer, et al. and incorporated herein by reference in its entirety. Another type of left lead adapted for placement in the coronary vasculature is that disclosed in U.S. Pat. No. 7,532,939, issued to Sommer, et al. and also incorporated herein by reference in its entirety. The side helixes from Sommer cannot be used to solely attach to epicardial tissue since the free end of the Sommer side helix is configured to engage thinner tissue for coronary vein fixation.

Additional designs for a side-helix leads are disclosed in U.S. Pat. No. 5,443,492, issued to Stokes, et al. U.S. Pat. No. 7,529,584, issued to Laske, et al, U.S. Pat. No. 7,313,445, issued to McVenes, et al., U.S. Pat. No. 6,493,591, issued to Stokes, U.S. Pat. No. 6,556,874, issued to Audoglio, all of which are incorporated herein in their entireties.

It is desirable to develop a medical electrical lead that minimizes trauma to the tissue and solely attaches to the epicardial tissue.

SUMMARY

The present disclosure comprises an implantable medical device that includes a housing, a processor disposed within the housing, and a medical electrical epicardial lead connected to the processor through a connector module. The epicardial lead is used to sense cardiac signals from tissue of a patient. The lead comprises an insulative lead body that includes a proximal end and a distal end, at least one conductor disposed in the lead body, and a side helical fixation member, disposed a distance from the distal end, the side helical fixation member. The side helical fixation member comprises a set of windings configured to wrap around the lead body circumference. The side helical fixation member includes a distal tip comprising a sharpened elongated flat free end that is perpendicular to the lead body and angled toward an inside of the set of windings. In response to the sensed cardiac signal, the device delivers electrical pulses through the epicardial lead.

The epicardial lead of the present disclosure resides solely epicardially and allows fixation more proximal on the lead body compared to the epicardial lead of Stokes et al. The lead stays only on the epicardial surface since the side helical member attaches or grabs the outer surface of the epicardium and cannot pass into the myocardium due to the tissue being wedged therein. The lead body and electrodes remain between the pericardial sac layer and the epicardium. The epicardial lead of the present disclosure allows a distal defibrillation electrode and a left ventricle pace/sense electrode to be placed along a path extending from the subxiphoid access location.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

Figure 1A:
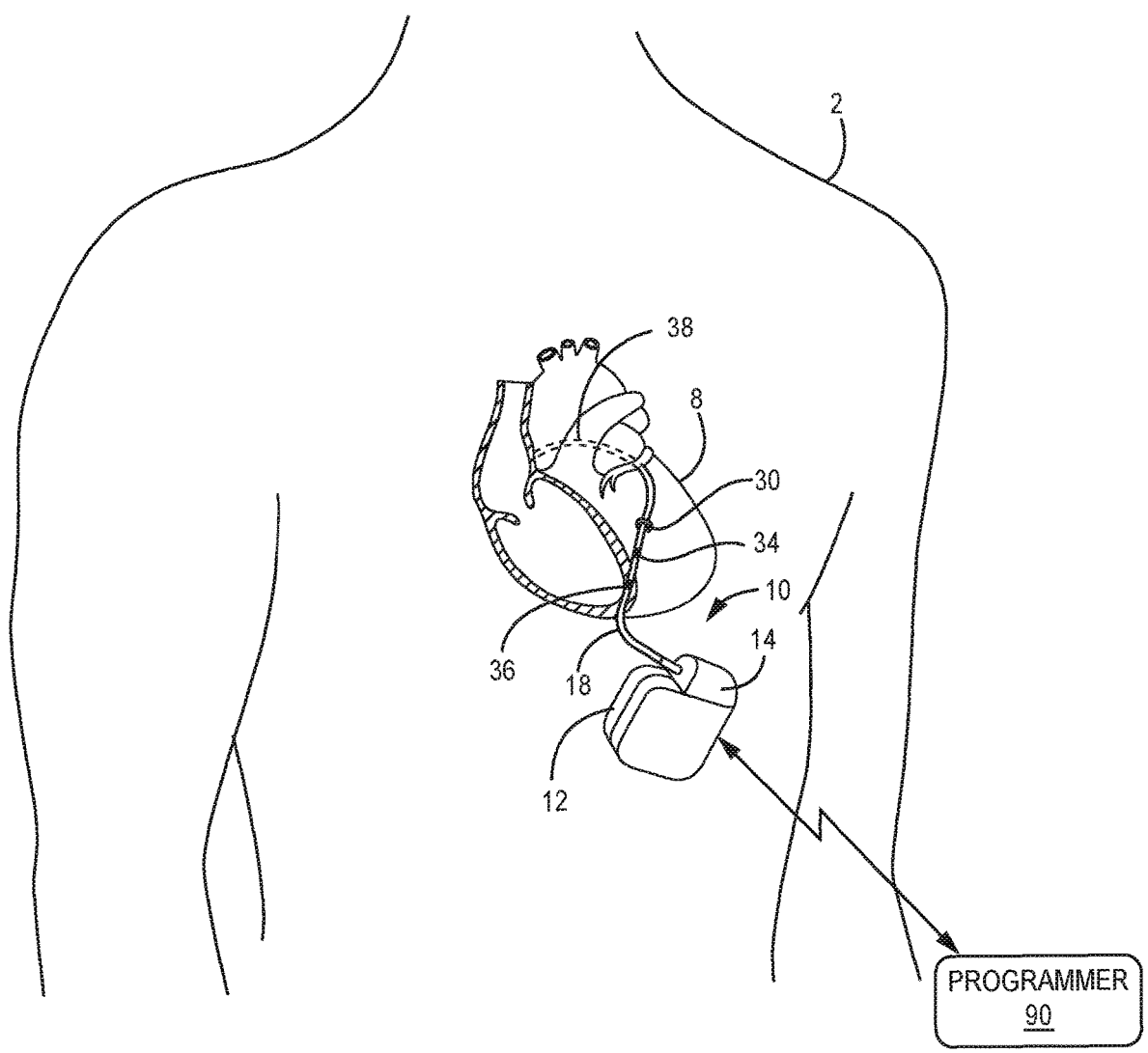
FIG. 1A is a conceptual schematic view of a patient with an implantable medical device in which a medical electrical lead extends therefrom.

One or more embodiments relate to an implantable medical device that includes a medical electrical epicardial lead. The lead includes (a) an insulative lead body that includes a proximal end and a distal end, (b) at least one conductor disposed in the lead body, and (c) a side helical fixation member, disposed a distance from the distal end. The side helical fixation member comprises a set of windings configured to wrap around the lead body circumference. The side helical fixation member further includes a distal tip comprising a sharpened elongated flat free end that is perpendicular to the lead body and angled toward inside of the set of windings. The sharpened elongated flat free end is configured to attach solely to epicardial tissue. In particular, the epicardial lead of the present disclosure is configured for deeper tissue engagement than other leads (e.g. U.S. Pat. No. 8,755,909 B2 to Sommer et al.) that are configured for attachment to thinner tissue such as the inside of coronary veins.

Skilled artisans will appreciate that the epicardial lead, disclosed herein, can be used for delivery of therapies such as cardioresynchronization therapy (CRT), defibrillation, and/or any bradycardia indication. In particular, the epicardial lead utilizes a lumenless lead body design, distal high voltage coil to be positioned in the superior region of the pericardial space (i.e. transverse sinus) and fixated with a side fixation helix just proximal to the high voltage coil into the epicardial surface of the posterior left ventricle (LV). Either one or two ring electrodes are positioned just proximal to the side fixation helix to provide ventricular pacing and sensing with additional atrial sensing in the integrated bipolar vector.

Placement of the epicardial lead can be performed using a telescoping catheter without performing a thoracotomy, which can be painful and potentially cause a patient to develop a pneumonia. Moreover, no pleural breach is required to perform delivery of the lead described herein. Consequently, only a single day of treatment in a hospital setting may be needed which is similar to placement of an endocardial lead for CRT (e.g. left ventricular only pacing, biventricular pacing etc.). General anesthesia is typically unnecessary for this method thereby further reducing complications associated with surgery. Epicardial leads can be beneficial to patients in which vascular access is less of an option. Moreover, epicardial leads have unrestricted access to optimal sites on the left ventricle or other cardiac tissue sites for delivery of electrical stimulation which may enhance therapies such as CRT, defibrillation, or delivery of pacing pulses.

The following description is merely exemplary in nature and is not intended to limit the present disclosure, application, or uses. The devices described herein include an exemplary number of leads, etc. One will understand that the components, including number and kind, may be varied without altering the scope of the disclosure. Also, devices according to various embodiments may be used in any appropriate diagnostic or treatment procedure, including a cardiac procedure. The epicardial leads disclosed herein are typically chronically implanted in a patient.

Figure 1B:
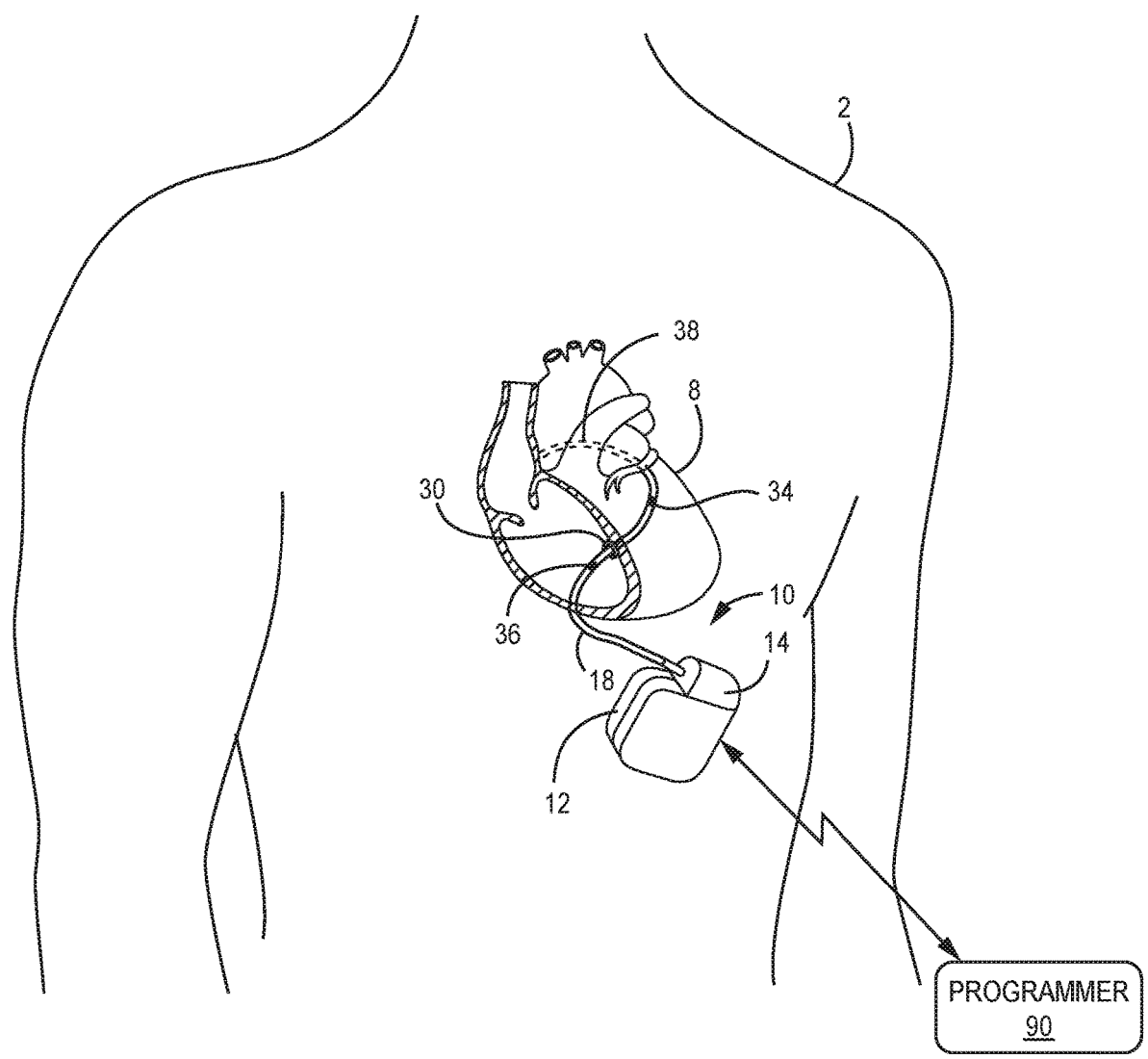
FIG. 1B is a conceptual schematic view of a patient with an implantable medical device in which a medical electrical lead extends therefrom.
Figure 3:
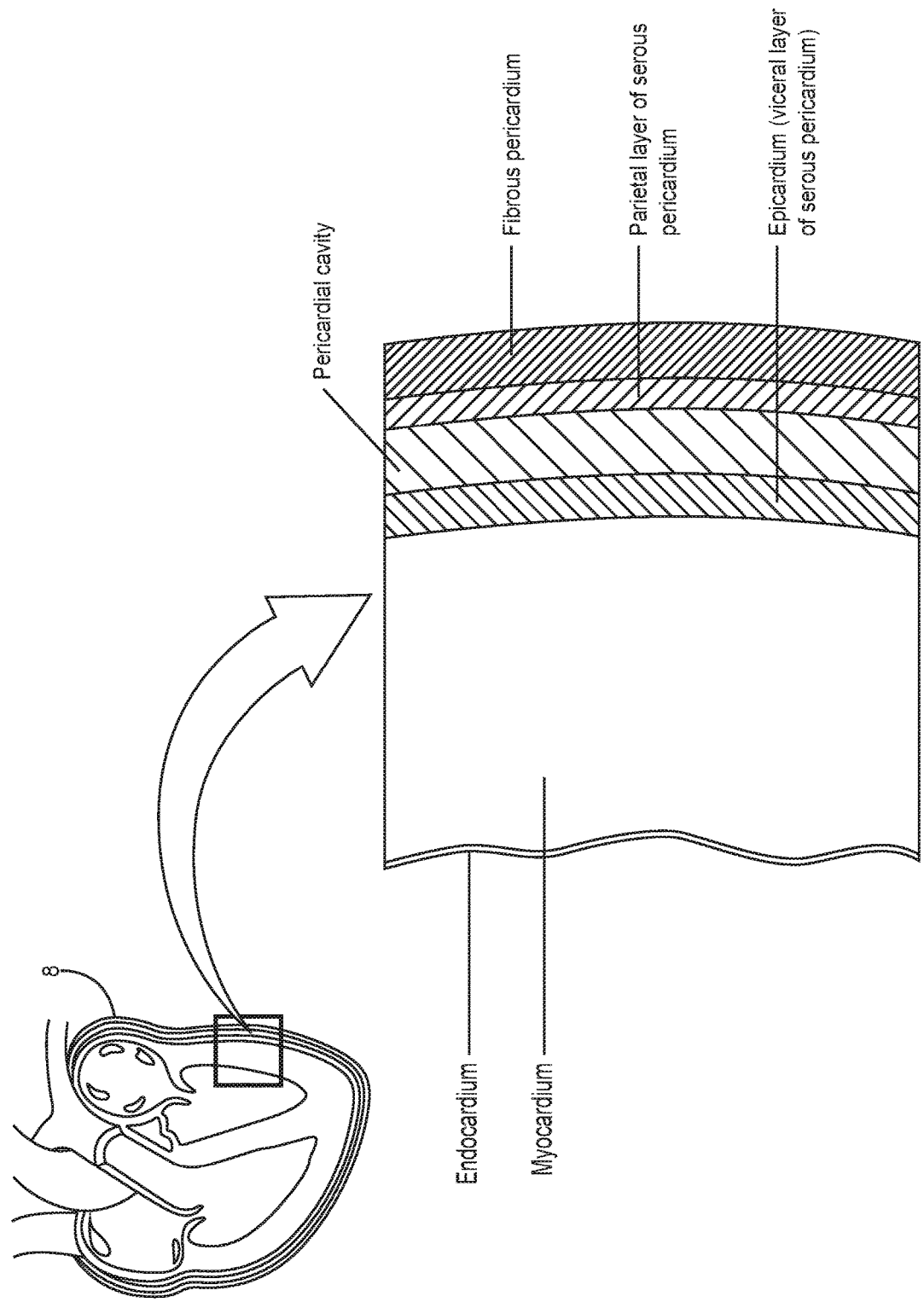
FIG. 3 is a schematic view of a heart and a cross-section of heart tissue.
Figure 7:
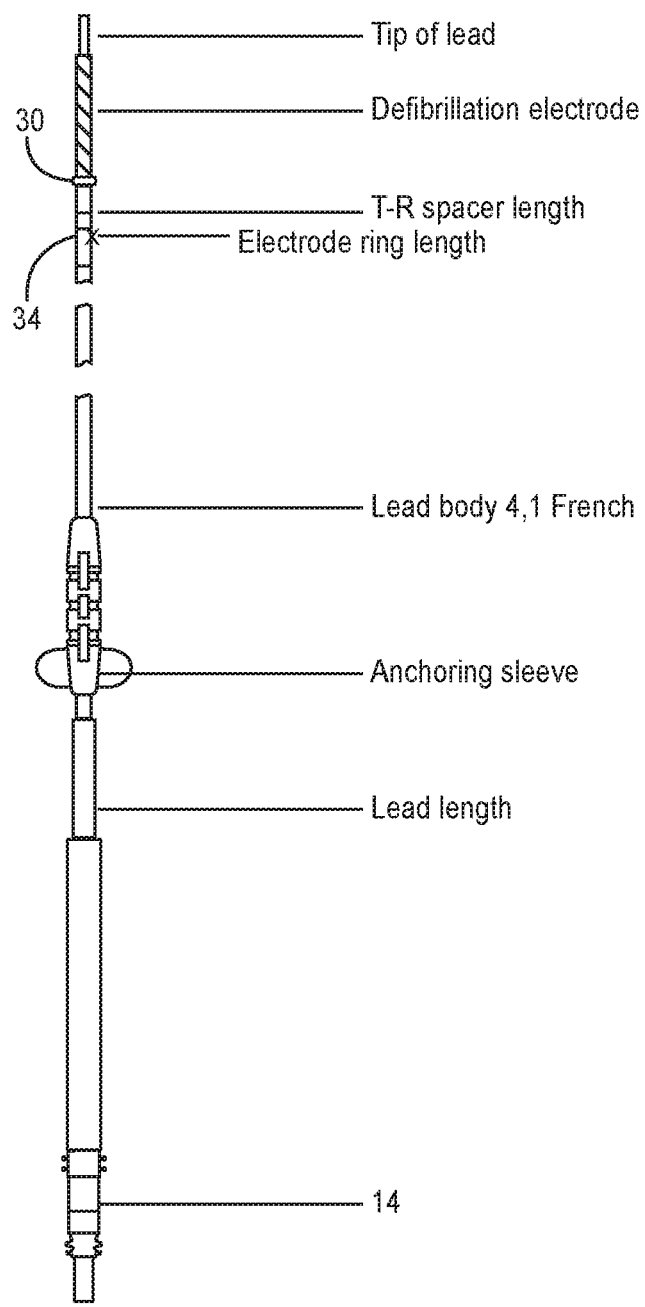
FIG. 7 is a schematic view of an elongated epicardial lead.

FIGS. 1A-1B depict a medical device system 10 coupled to a heart 8 of a patient 2 by way of an epicardial lead 18, which is stabilized through an anchoring sleeve, depicted in FIG. 7, used in a conventional fashion to stabilize the lead at the insertion site. Referring briefly to FIG. 3, heart 8 comprises endocardium, myocardium, epicardium (i.e. visceral layer of serous pericardium), pericardial cavity, parietal layer of serous pericardium and fibrous pericardium. Each layer exhibits a different level of resistance to force that may be used to pierce one or more layers in order to affix an implantable medical device to tissue.

Figure 4:
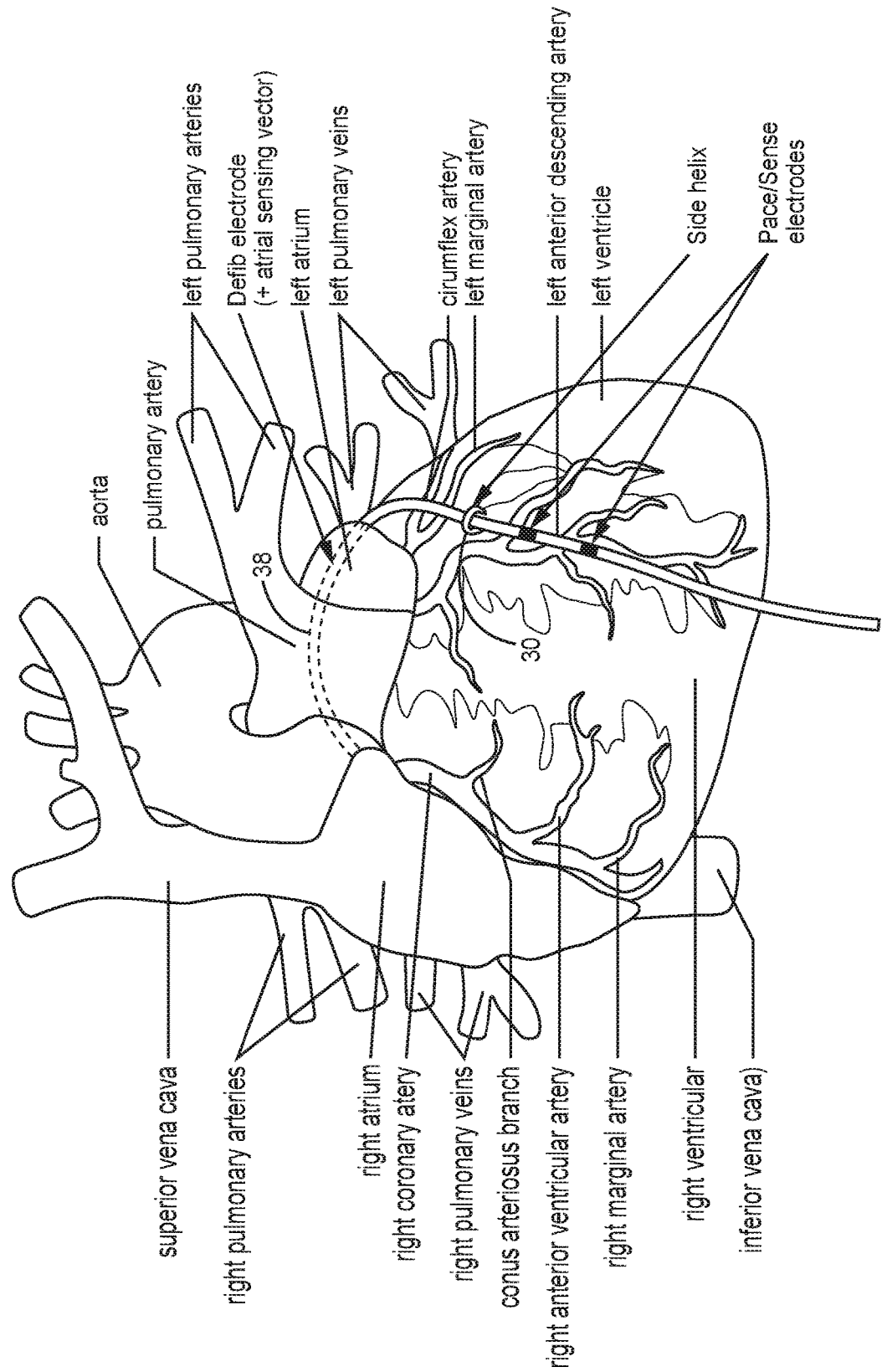
FIG. 4 is a conceptual schematic view of an implantable medical device in which a medical electrical lead extends therefrom as depicted in FIG. 1A.

FIG. 1A depicts an epicardial lead 18 placed on heart 8 as shown relative to FIG. 4 for delivery of CRT. For example, lead 18 includes a set of electrodes comprising pace and or sense electrodes 34, 36 and a defibrillation electrode 38. defibrillation electrode 38 can optionally include an atrial sensing vector. Defibrillation electrode 38 is placed over the pulmonary artery to the right atrium. The lead 18 further includes a left ventricular pace/sense electrode 34 placed on the left ventricle, a right ventricular pace sense electrode 36. A side helical fixation member 30, coupled to the epicardial lead 18, is attached to the epicardium.

Figure 5:
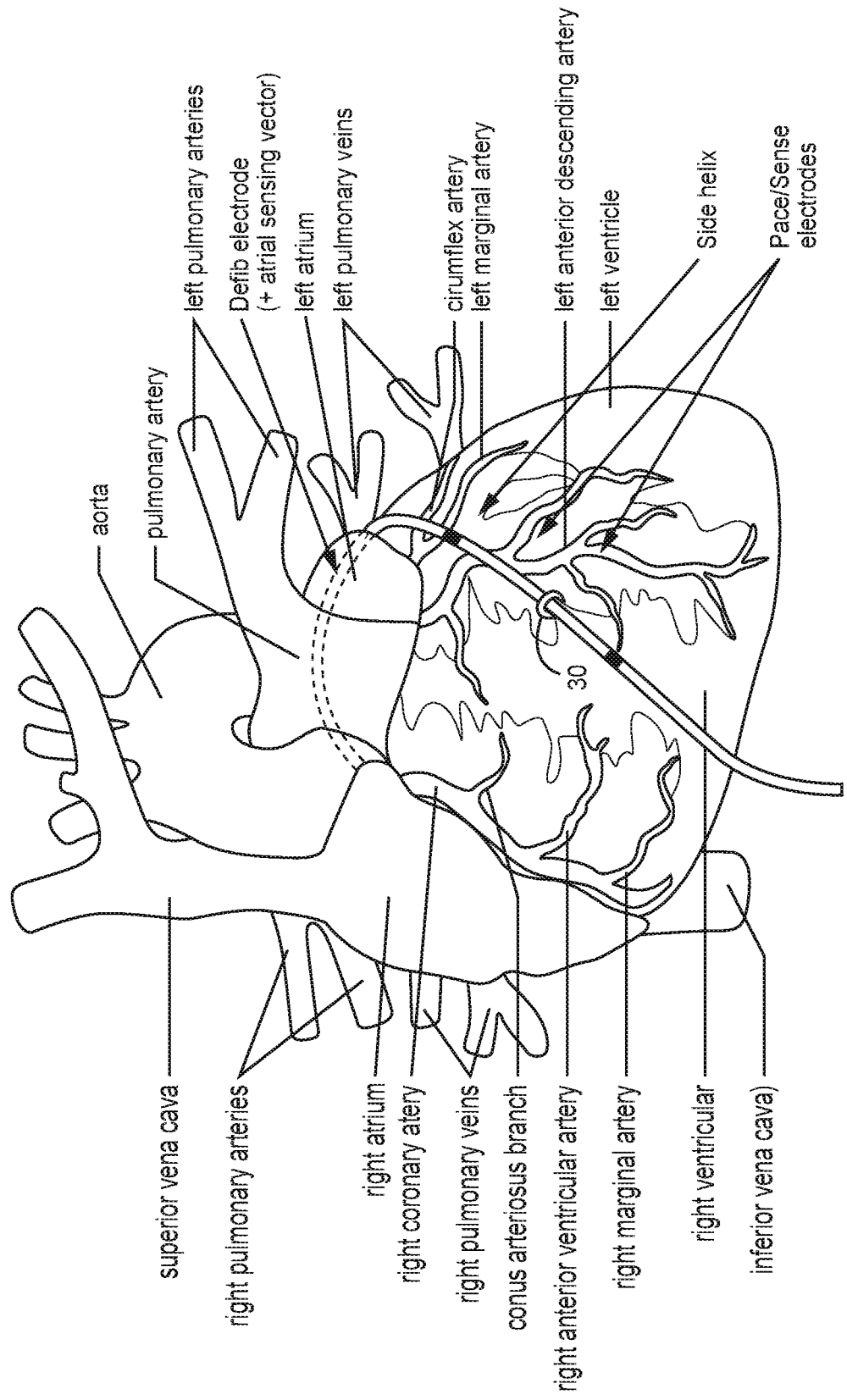
FIG. 5 is a conceptual schematic view of an implantable medical device in which a medical electrical lead extends therefrom as depicted in FIG. 1B.

FIG. 1B depicts an epicardial lead 18 placed on heart 8 as shown relative to FIG. 5 for delivery of CRT. In particular, FIG. 1B depicts a left ventricular pace/sense electrode 34 near left ventricle, a right ventricular pace sense electrode 36 with a side helical fixation member therebetween along an epicardial lead 18.

A medical device system 10 includes a medical device housing 12 having a connector module 14 (e.g. international standard (IS)-4, defibrillation (DF)-1, DF-4 etc.) that electrically couples various internal electrical components housed in medical device housing 12 to a proximal end of a medical electrical lead 18. A medical device system 10 may comprise any of a wide variety of medical devices that include one or more medical lead(s) 18 (e.g. bipolar side helix lead) and circuitry coupled thereto. An exemplary medical device system 10 can take the form of an implantable cardiac pacemaker, an implantable cardioverter, an implantable defibrillator, an implantable cardiac pacemaker-cardioverter-defibrillator (PCD), a neurostimulator, a tissue and/or muscle stimulator. IMDs are implanted in a patient in an appropriate location. Exemplary IMDs are commercially available as including one generally known to those skilled in the art, such as the Medtronic CONCERTO™, SENSIA™, VIRTUOSO™, RESTORE™, RESTORE ULTRA™, VIVA™ sold by Medtronic, Inc. of Minnesota. Aspects of the disclosure can be used with many types and brands of IMDs. Medical device system 10 may deliver, for example, pacing, cardioversion or defibrillation pulses to a patient via electrodes disposed on distal end of one or more lead(s). Specifically, the lead may position one or more electrodes with respect to various cardiac locations so that medical device system 10 can deliver electrical stimuli to the appropriate locations.

Figure 6:
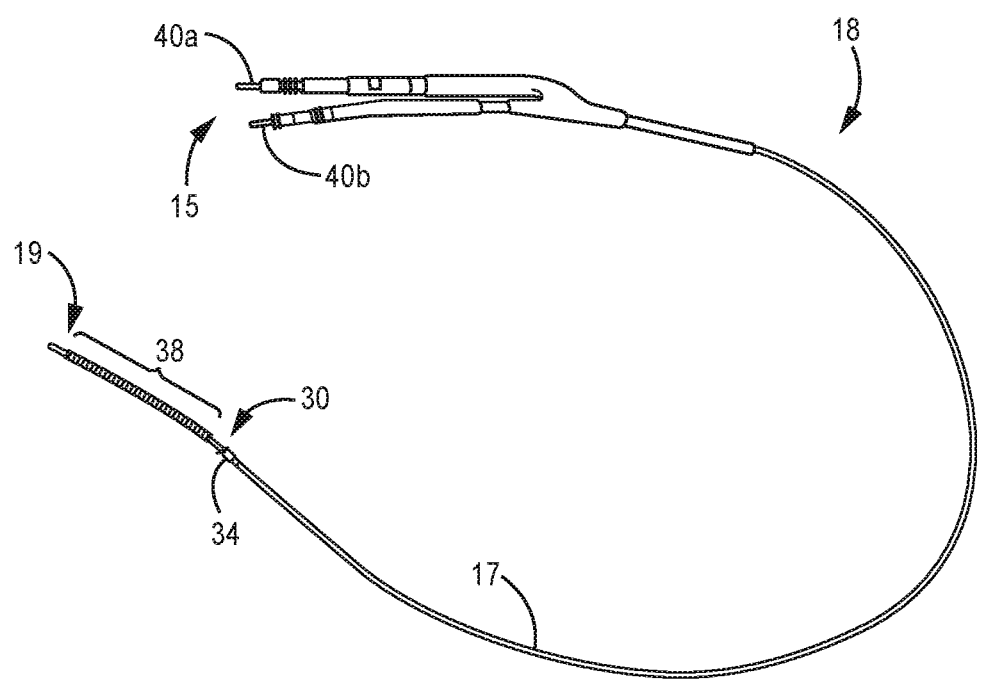
FIG. 6 is a schematic view of an elongated bipolar epicardial lead.
Figure 8A:
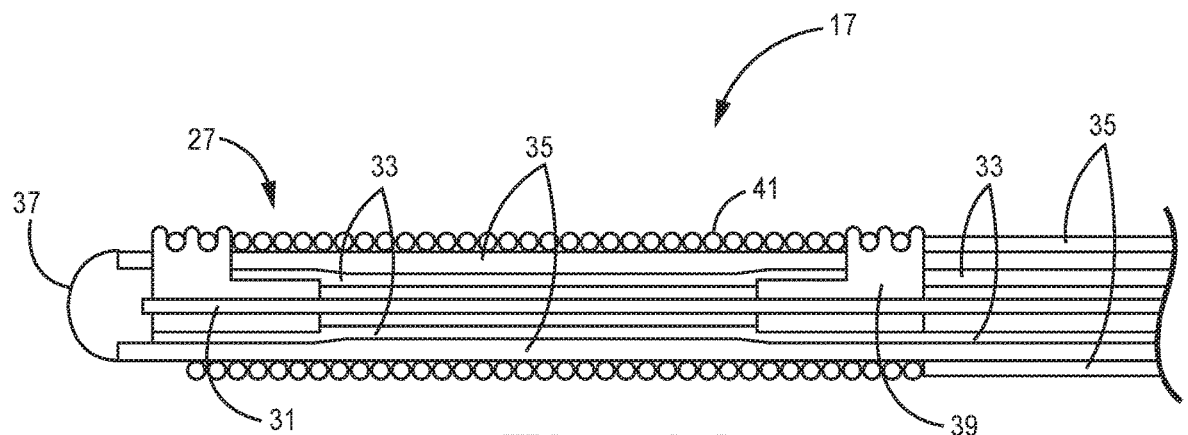
FIG. 8A depicts a lead body without a side helix fixation member.
Figure 8B:
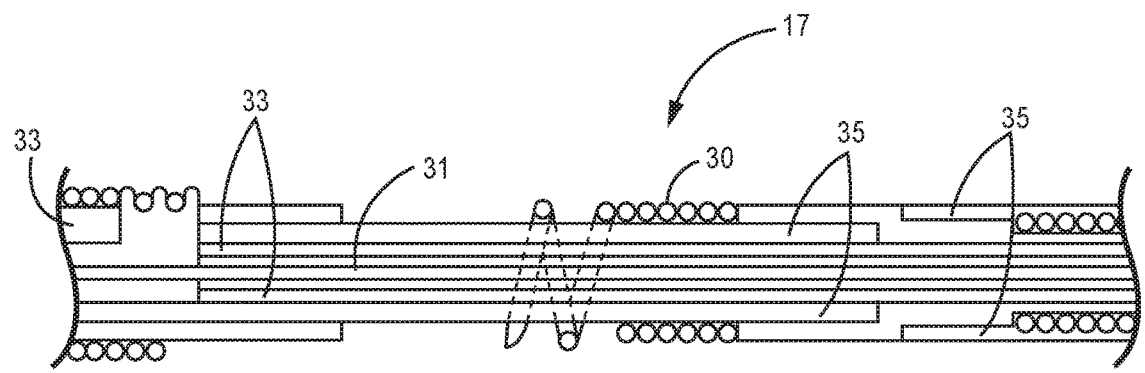
FIG. 8B depicts a lead body with a side helix fixation member.

Lead 18 includes an elongated lead body 17 (shown in greater detail in FIG. 6 and FIGS. 8A-8B). Lead 18 utilizes a lumenless lead body design, distal high voltage coil to be positioned in the superior region of the pericardial space (i.e. transverse sinus) and fixated with a side fixation helix just proximal to the high voltage coil into the epicardial surface of the posterior LV. Lead body 18 extends from a proximal end 15 to a distal end 19 at the tip 37 of the lead 18. In one or more embodiments, lead body 17 can be size 4 or less French. One or more other embodiments involve lead body 17 sizes up to 9/10 French since an increased diameter can increase electrode surface area for defibrillation. Lead body 17 can include one or more jacketed elongated conductive elements 40a,b. A jacket 35 (also referred to as a layer, longitudinal element, coating, tubing etc.) extends longitudinally and around the conductive elements 40a,b to insulate one or more conductive elements 40a,b.

Electrically conductive elements 40a,b for lead 18 can include coils, wires, coil wound around a filament, cables, conductors or other suitable members. Conductive elements 40 can comprise platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. Electrically conductive element 40a, is covered, or substantially covered, longitudinally with a jacket (also referred to as a layer, a longitudinal element, a longitudinal member, a coating, a tubular element, a tube or a cylindrical element). Typically, the outer surface of electrodes such as the ring electrode, the tip electrode, and the defibrillation coil 27 are exposed or not covered by a jacket or layer so that electrodes can sense and/or deliver electrical stimuli to tissue of a patient.

Fixation mechanism 30 (e.g. side helix) or side helical member can be located at the distal end of lead 18 to attach the lead 18 to epicardial tissue. Referring to FIGS. 9A-9F, various views of the side helical fixation member 30 are shown. The side helical member 30 is configured such that it extends radially outward from the lead for a short distance and then coils helically around at least a portion along the longitudinal axis of the lead body circumference. The location of the helical fixation member 30 is based on the specific application and intended cardiac anatomy. For small anatomies, such as pediatric patients, the helix location may range from about 3 cm to about 6 cm from the distal tip to allow positioning of a defibrillation electrode of about 2 cm to about 5 cm long. For large anatomies such as adult heart failure and dilated cardiomyopathies the helix location may range from 6 cm to 12 cm from the distal tip to allow positioning of a defibrillation electrode of 4 cm to 8 cm long and left ventricular/atrial pace sense electrode. The side helical member 30, for example, includes a helical pitch with an inner diameter of about 1 French or less up to equal to that of the lead body diameter (e.g. 3.2 French to 4.1 French for a 4.1 French lead body), an main outer diameter (OD) of about equal to the lead body outer diameter to 1.5 French larger (4.1 French to 5.5 French for a 4.1 French lead body), and a length of about 3.4 mm to about 4 mm in order to screw into tissue. Side helical fixation member 30 employs a right wound coil or spring configuration. A right wound coil or spring configuration involves right hand wound spring spirals which turns in the same direction as a right hand threaded screw. For example, a front point, on the spiral, travels up to the right, as shown in FIGS. 9B-9C. The side helical fixation member 30 includes a window portion 32 (also referred to as an open or cut-away portion) formed by length side $W_L$ and window width $W_W$. The window portion serves two functions. First, mechanical interlocking is achieved with the open window 32. For example, polyurethane is placed on the outside surface of a fused helical tubular section. The polyurethane is either melted and/or reflowed through the window portion 32 over the windings. Consequently, the side helical member 30 is locked or affixed to the lead body 17.

Second, window 32 allows the physician to visualize the turns of the side helix using the fluoroscopy during the implantation procedure. For example, the physician can position the lead, and, when ready, watch as the helix turns using the window portion 32 as a means to track turning of the side helical fixation member 30. Without fluoroscopy, either a videoscope is used to visualize turning of the side helix or lead body torque feedback is employed as described in U.S. patent application Ser. No. 14/696,242, entitled METHOD AND APPARATUS FOR DETERMINING SUITABILITY OF A LEAD IMPLANT LOCATION, incorporated by reference in its entirety herein.

Figure 9A:
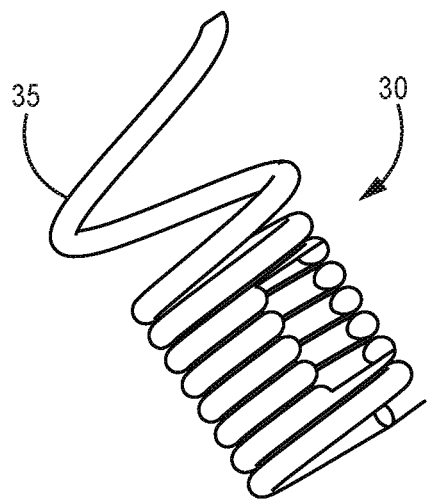
FIG. 9A depicts a schematic isometric view of the side helix fixation member having a portion or window open from a top view.
Figure 9B:
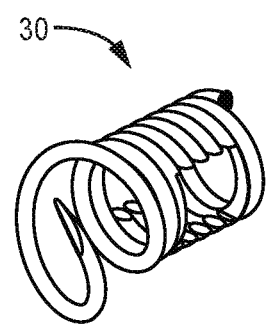
FIG. 9B depicts a schematic isometric view of the side helix fixation member having a portion or window cut-away from a side view.
Figure 9C:
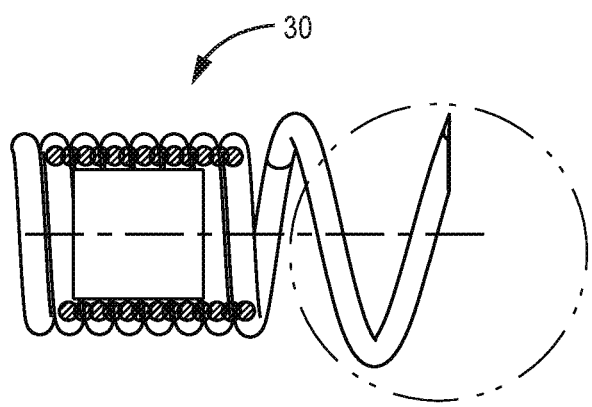
FIG. 9C depicts a cross-sectional view along a longitudinal axis of the side helix fixation member with a portion cut-away.
Figure 9D:
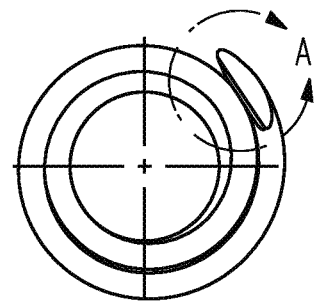
FIG. 9D is an orthographic view of the side helix fixation member depicted in FIG. 9C.
Figure 11A:
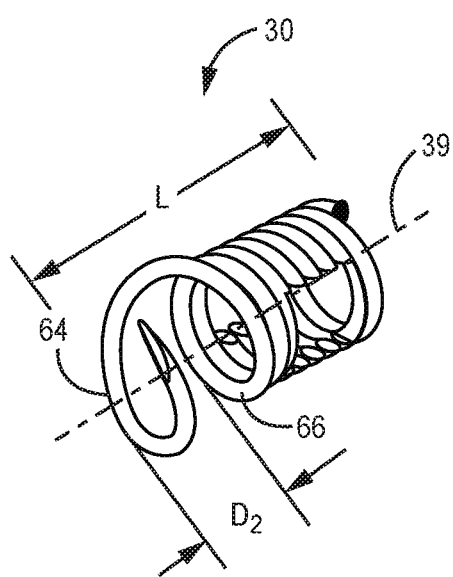
FIG. 11A depicts a schematic isometric view of the side helical fixation member and is compared to the conventional side helical fixation member of FIG. 10A.

In one or more embodiments of the side helical fixation member 30, depicted in FIG. 9A and FIG. 11A, includes a longitudinal length L that extends about 0.142 inches from the very distal end to the proximal end. Radial distances, denoted as A, B, in FIG. 11B for side helix are based on the outer diameter (OD) plus 30%, 60% and 90% of the wire diameter, respectively. Exemplary dimensions for A and B are 0.0620 inches and 0.046 inches, respectively.

Figure 10A:
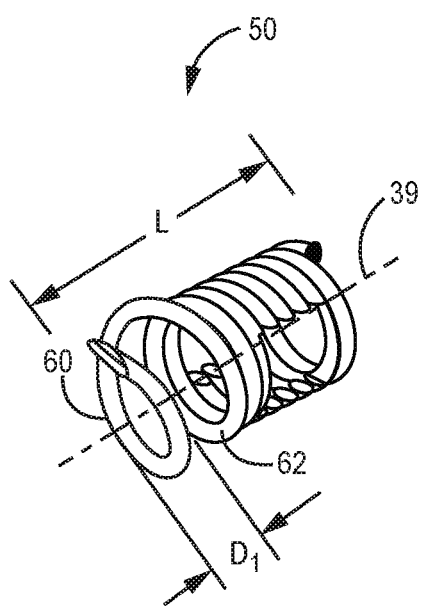
FIG. 10A depicts a schematic isometric view of a conventional side helical fixation member according to the prior art in which a distance D1 exists between the first and second winds.
Figure 10B:
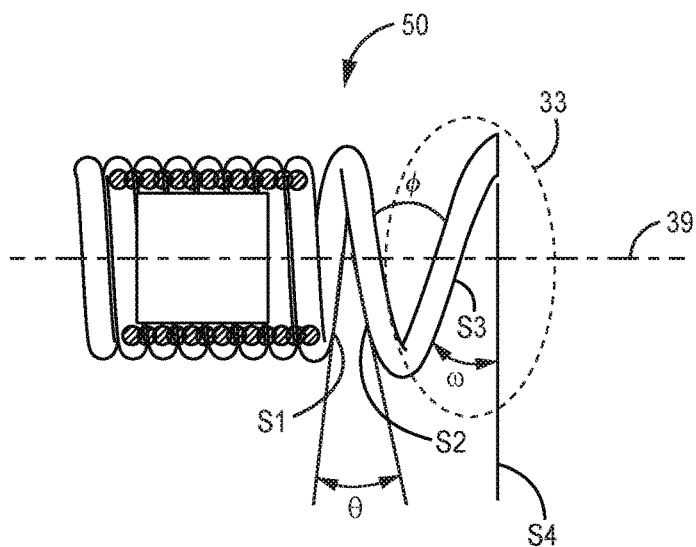
FIG. 10B depicts a cross-sectional view along a longitudinal axis of the conventional side helical fixation member shown in FIG. 10A, according to the prior art.
Figure 11B:
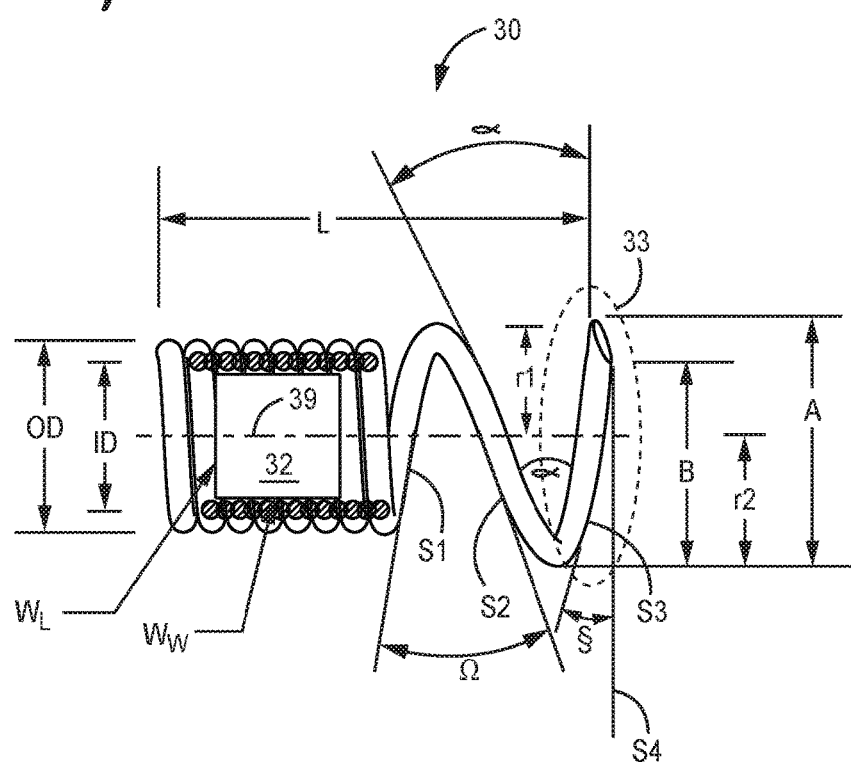
FIG. 11B depicts a cross-sectional view along a longitudinal axis of the side helical fixation member and is compared to the conventional side helical fixation member of FIG. 10A.
Figure 10C:
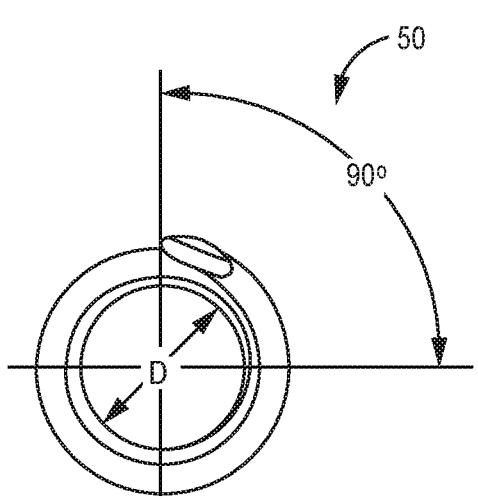
FIG. 10C is an orthographic view of the side helical fixation member depicted in FIG. 10B, according to the prior art.
Figure 11C:
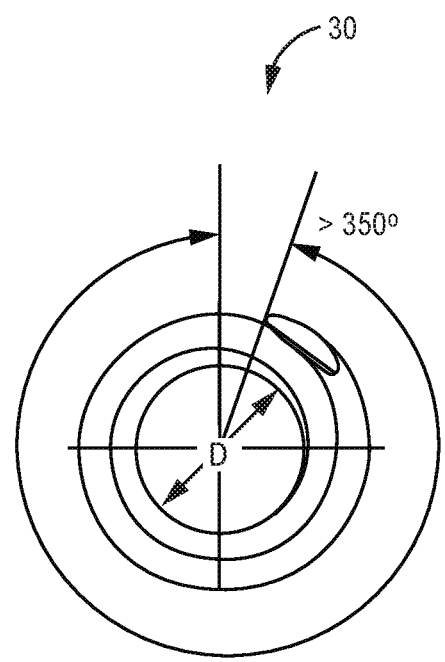
FIG. 11C is an orthographic view of the side helical fixation member depicted in FIG. 10B.

A side-to-side comparison is made between a conventional side helical fixation member 50, shown in FIGS. 10A-10C (prior art) and a side helical member 30 of the present disclosure shown in FIGS. 11A-11C. Referring to FIGS. 10A-10C, conventional side helix 50, shown and described in U.S. Pat. No. 7,860,580, issued to Sommer, was designed for coronary vein fixation. In particular, side helical member 50 is configured to engage thinner tissue along a concave surface such as the inner cylindrical surface of the coronary vein wall.

Side helical members 30, 50 extend a length L and comprise a set of windings configured to wrap around the circumference of lead body 17. A sharpened tip is located at a distal end of the side helical member 50. Side helical member 50 has a first wind 60 that extends an axial distance D1 to the second wind 62. The side helical member 30 shown in FIG. 11A has a first wind 64 that extends a distance D2 to the second wind 66. D1 is substantially less than distance D2. For example, referring to FIG. 10B, the first and second winds 60, 62 have radial dimensions of about 0.0337 inches and 0.0350 inches, respectively measured away from the center 39 of the helix barrel. In comparison, the first and second winds 64, 66 are about 0.036 inches and 0.040 inches, respectively.

Other differences exist between side helical members 30, and 50. For example, referring to FIG. 10B, side helical member 50 has an angle theta ($\ominus$) into the first wind, defined by surfaces S1 and S2. Angle $\ominus$ is considered shallow (e.g. about 18°). In contrast, side helical member 30 shown in FIG. 11B has a steep angle omega ($\Omega$) into the first wind. Angle $\Omega$ is defined by surfaces S1 and S2, which is about 30°. In one or more other embodiments, $\Omega$ can be 25° or more.

In addition, side helical member 50 shown in FIG. 10B has a steep angle phi ($\phi$) (e.g. 25°, 30°, 35° etc.) into the tip defined by surfaces S3 and S2 while side helical member 30 comprises angle alpha (α) defined by surfaces S2 and S3. Alpha α is less than phi φ. For example, alpha α can be less than 25°, equal to or less than 20°, equal to or less than 18°. Yet another difference exists by the angle ώ (FIG. 10B) and angle § (FIG. 11B) formed between surface S3 and line S4. Line S4 is perpendicular to the center 39 of the barrel. Angle ώ is 20° or more while angle § is 15° or less.

Additionally, side helical member 50 shown in FIG. 10B possesses a helical tip of about 0.039 inches measured from a longitudinal axis 39 or centerline of the helical member 50 to the tip whereas side helical member 30 possesses a substantially greater helical tip of about 0.056 inches measured from a longitudinal axis. Moreover, the maximum diameter from the longitudinal axis of the helical member is 0.074 inches for helical member 50 as compared to 0.096 inches for side helical member.

Referring to FIGS. 10B-10C, the angle of the free end 33 or kick-out of helical member 50 is shown as being a small angle (e.g. less than 90°). In contrast, the angle of the free end or kick-out shown in FIG. 11C is greater than 350° for the helical fixation member 30. Additionally, on the last wind of side helical member 30, a very flat pitch (denoted as § in FIG. 11B) is used on the tip to increase stability and reduce auto-rotation (i.e. turning of the helix with tensile force). In comparison, side helical member 50 uses a 45° angle and has a high degree of autorotation. In one or more embodiments, the side helical member 30 is not electrically active. In another embodiment, side helical member 30 can be configured to be electrically active. Exemplary wire gauge used is 26-36 AWG bare wire or that optionally includes titanium nitride coating having a one to one ratio. Side helical fixation member 30 is configured to have a minimum of a ¾ turn to achieve excellent fixation on a tangent to the heart surface. Helical fixation member 30 enters and passes through and out of the epicardium.

In addition to side helical member 30, lead 18 includes electrodes. Optionally, one or more of the electrodes, such as on the epicardial lead, can be drug eluting such as that which is disclosed in U.S. 20140005762 filed Jun. 29, 2012, assigned to the assignee of the present invention, is incorporated by reference in its entirety. Additionally, the tip and ring electrodes can be coated with titanium nitride (TiN). Optionally, a flexible anode ring electrode can be included on the lead. The flexible anode ring electrode can comprise bare platinum/iridium (Pt/Ir). The electrodes can take the form of ring and barrel shaped electrodes, respectively, as described in U.S. Pat. No. 8,825,180 by Bauer, et al., incorporated herein by reference in its entirety. The electrodes can include steroid (e.g. beclomethasone) eluting MCRD's. Other known electrode designs may of course be substituted.

Exemplary lead insulation that can be used in conjunction with the present disclosure are shown and described with respect to U.S. Pat. No. 8,005,549 issued Aug. 23, 2011, U.S. Pat. No. 7,783,365 issued Aug. 24, 2010, and assigned to the assignee of the present invention, the disclosure of which are incorporated by reference in their entirety herein. ATTAIN PERFORMA™ Model 4298 quadripolar lead insulation is another exemplary insulative material that can be used.

Examples of connector modules may be seen with respect to U.S. Pat. No. 7,601,033 issued Oct. 13, 2009, U.S. Pat. No. 7,654,843 issued Feb. 2, 2010, and assigned to the assignee of the present invention, the disclosure of which are incorporated by reference in their entirety herein. Connector module 14, as illustrated, takes the form of a DF quadripolar connecter, but any appropriate connector mechanism (e.g. IS1/DF1 as bipolar/unipolar connectors etc.) may be substituted. Connector module 14 electrically couples a proximal end of each lead to various internal electrical components of implantable medical device 10 through a connector or set screw.

Figure 2:
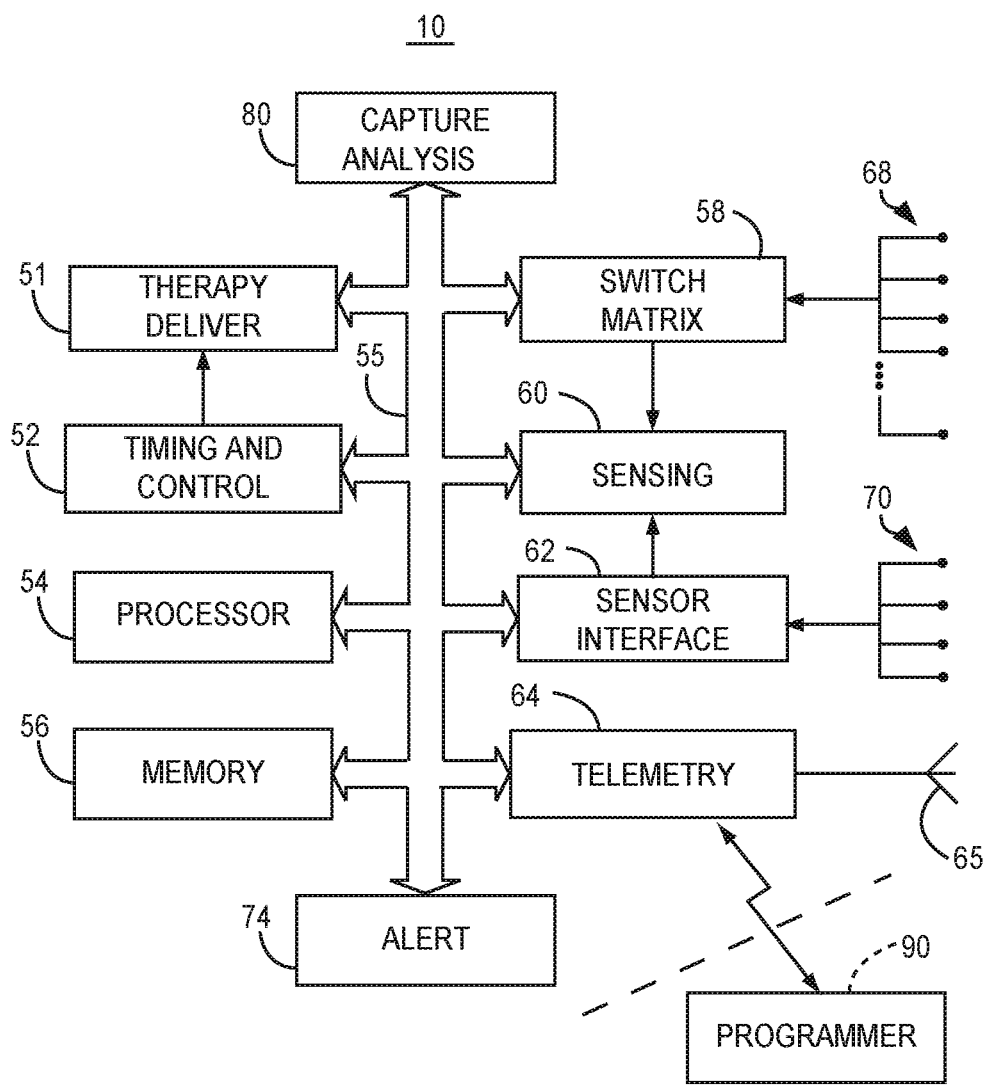
FIG. 2 is a functional block diagram of the IMD shown in FIG. 1.

FIG. 2 is a functional block diagram of IMD 10. IMD 10 generally includes timing and control circuitry 52 and an operating system that may employ processor 54 for controlling sensing and therapy delivery functions in accordance with a programmed operating mode. Processor 54 and associated memory 56 are coupled to the various components of IMD 10 via a data/address bus 55. Processor 54, memory 56, timing and control 52, and capture analysis module 80 may operate cooperatively as a controller for executing and controlling various functions of IMD 10.

Processor 54 may include any one or more of a microprocessor, a controller, a digital state machine, a digital signal processor (DSP), an application specific integrated circuit (ASIC), a field-programmable gate array (FPGA), or equivalent discrete or integrated logic circuitry. In some examples, processor 54 may include multiple components, such as any combination of one or more microprocessors, one or more controllers, one or more DSPs, one or more ASICs, or one or more FPGAs, as well as other discrete or integrated logic circuitry. The functions attributed to processor 54 herein may be embodied as software, firmware, hardware or any combination thereof. In one example, capture analysis module 80 and/or sensing module 60 may, at least in part, be stored or encoded as instructions in memory 56 that are executed by processor 54.

IMD 10 includes therapy delivery module 51 for delivering a therapy in response to determining a need for therapy based on sensed physiological signals. Therapy delivery module 50 includes a signal generator for providing electrical stimulation therapies, such as cardiac pacing or arrhythmia therapies, including CRT. Therapies are delivered by module 50 under the control of timing and control 52. Therapy delivery module 50 is coupled to two or more electrodes 68 via a switch matrix 58 for delivering pacing pulses to the heart. Switch matrix 58 may be used for selecting which electrodes and corresponding polarities are used for delivering electrical stimulation pulses. Electrodes 68 may correspond to the electrodes 12, 30, 34, 36 and 38 shown in FIG. 1 or any electrodes coupled to IMD 10.

Timing and control 52, in cooperation with processor 54 and capture analysis module 80, control the delivery of pacing pulses by therapy delivery 50 according to a programmed therapy protocol, which includes the option of multi-site pacing wherein multiple pacing sites along a heart chamber are selected using methods described herein. Selection of multiple pacing sites and control of the pacing therapy delivered may be based on results of activation time measurements or an anodel capture analysis algorithm or a combination of both. As such, capture analysis module 80 is configured to determine pacing capture thresholds and detect the presence of anodel capture for determining both anodel and cathodal capture thresholds for a given pacing vector in some embodiments.

Electrodes 68 are also used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrodes 68 are coupled to sensing module 60 via switch matrix 58. Sensing module 60 includes sense amplifiers and may include other signal conditioning circuitry and an analog-to-digital converter. Cardiac EGM signals (either analog sensed event signals or digitized signals or both) may then be used by processor 54 for detecting physiological events, such as detecting and discriminating cardiac arrhythmias, determining activation patterns of the patient's heart, measuring myocardial conduction time intervals, and in performing anodel capture analysis and pacing capture threshold measurements as will be further described herein.

IMD 10 may additionally be coupled to one or more physiological sensors 70. Physiological sensors 70 may include pressure sensors, accelerometers, flow sensors, blood chemistry sensors, activity sensors or other physiological sensors for use with implantable devices. Physiological sensors may be carried by leads extending from IMD 10 or incorporated in or on the IMD housing. Sensor interface 62 receives signals from sensors 70 and provides sensor signals to sensing module 60. In other embodiments, wireless sensors may be implanted remotely from IMD 10 and communicate wirelessly with IMD 10. IMD telemetry circuitry 64 may receive sensed signals transmitted from wireless sensors. Sensor signals are used by processor 54 for detecting physiological events or conditions.

The operating system includes associated memory 56 for storing a variety of programmed-in operating mode and parameter values that are used by processor 54. The memory 56 may also be used for storing data compiled from sensed signals and/or relating to device operating history for telemetry out upon receipt of a retrieval or interrogation instruction. The processor 54 in cooperation with therapy delivery module 50, sensing module 60 and memory 56 executes an algorithm for measuring activation times for selecting pacing sites for delivering multi-site pacing.

A capture analysis algorithm may be stored in memory 56 and executed by processor 54 and/or capture analysis module 80 with input received from electrodes 68 for detecting anodel capture and for measuring pacing capture thresholds. Microprocessor 54 may respond to capture analysis data by altering electrode selection for delivering a cardiac pacing therapy. Data relating to capture analysis may be stored in memory 56 for retrieval and review by a clinician and that information may be used in programming a pacing therapy in IMD 10.

IMD 10 further includes telemetry circuitry 64 and antenna 65. Programming commands or data are transmitted during uplink or downlink telemetry between IMD telemetry circuitry 64 and external telemetry circuitry included in programmer 90.

Programmer 90 may be a handheld device or a microprocessor based home monitor or bedside programming device used by a clinician, nurse, technician or other user. IMD 10 and programmer 90 communicate via wireless communication. Examples of communication techniques may include low frequency or radiofrequency (RF) telemetry using Bluetooth or MICS but other techniques may also be used.

A user, such as a physician, technician, or other clinician, may interact with programmer 90 to communicate with IMD 10. For example, the user may interact with programmer 90 to retrieve physiological or diagnostic information from IMD 10. Programmer 90 may receive data from IMD 10 for use in electrode selection for CRT, particularly data regarding cathodal and anodel capture thresholds and other measurements used in electrode selection such as hemodynamic measurements and LV activation times. A user may also interact with programmer 90 to program IMD 10, e.g., select values for operational parameters of the IMD. For example, a user interacting with programmer 90 may select programmable parameters controlling a cardiac rhythm management therapy delivered to the patient's heart 8 via any of electrodes 68.

Processor 54, or a processor included in programmer 90, is configured to compute battery expenditure estimates in some embodiments. Using measured pacing capture thresholds and lead impedance measurements, along with other measured or estimated parameters, the predicted battery longevity of the IMD 10 may be computed for different pacing configurations. This information may be used in selecting or recommending a multi-site pacing configuration. As such, IMD 10 is configured to perform lead impedance measurements and determine other parameters required for estimated energy expenditure calculations, which may include but are not limited to a history of pacing frequency, capture thresholds, lead impedances, and remaining battery life.

While not shown explicitly in FIG. 2, it is contemplated that a user may interact with programmer 90 remotely via a communications network by sending and receiving interrogation and programming commands via the communications network. Programmer 90 may be coupled to a communications network to enable a clinician using a computer to access data received by programmer 90 from IMD 10 and to transfer programming instructions to IMD 10 via programmer 90. Reference is made to commonly-assigned U.S. Pat. No. 6,599,250 (Webb et al.), U.S. Pat. No. 6,442,433 (Linberg et al.) U.S. Pat. No. 6,622,045 (Snell et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, hereby incorporated herein by reference in their entirety.

FIG. 10 is a plan view of an exemplary medical electrical lead connected through to a delivery device or guide catheter such as the ATTAIN CATHETER® developed and sold by Medtronic, Inc. of Minneapolis, Minn. The lead is configured to deliver electrical stimulation to tissue and/or sense signals from the tissue. The lead includes proximal end and a distal end with a lead body therebetween that generally defines a longitudinal axis. At the proximal end is located an in-line bipolar connector assembly 14. The distal end, which includes set of electrodes (e.g., can be configured in many different ways to ensure the lead stays in position to deliver electrical therapy to cardiac tissue.

Figure 13:
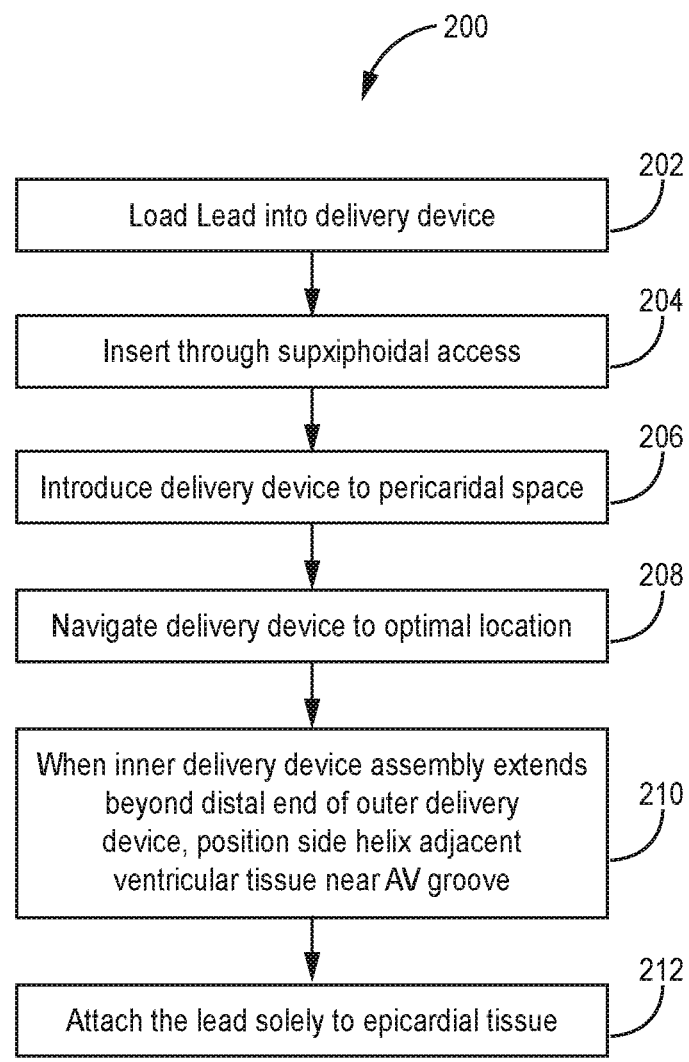
FIG. 13 is a flow diagram of a method of implanting an epicardial medical electrical lead.

FIG. 13 depicts a minimally invasive pericardial access method 200 for delivering an epicardial lead 18 to any location on the surface of the heart. The guiding catheter 100, described herein, is configured to place the epicardial lead 18 on the outer surface of the ventricle (left ventricle (LV), right ventricle (RV)) or the atrium (left atrium (LA), right atrium (RA)) without use of negative pressure or suction to place the lead. In one or more embodiments, catheter 100 is designed as a fixed shape to wrap around the surface of the heart in order to reach atria or ventricle (LV, RV). Guide catheter 100 can be configured to include a single catheter or telescoping catheter system comprising inner and outer catheters (e.g. ATTAIN COMMAND™ (e.g. outer catheter) and ATTAIN SELECT II™ (e.g. inner catheter). Exemplary delivery devices can also be used such as the ATTAIN PERFORMA™ Model 4298 commercially available from Medtronic. Another exemplary delivery device may be seen with respect to U.S. Pat. No. 9,155,868 issued May 5, 2015, and assigned to the assignee of the present invention, the disclosure of which is incorporated by reference in its entirety herein. Another exemplary delivery system is configured to stabilize the lead and provide space for the lead delivery catheter for lead 18 placement on the epicardial surface. The delivery system can comprise of a telescoping catheter system. The outer catheter has a balloon on the distal tip to both stabilize the catheter and also provide support and space for the inner catheter. The inner catheter telescopes through and extends beyond the distal tip of the outer balloon catheter and has a 90 degree or more curve on the distal end that directs the lead into the correct position for engagement into the epicardial surface.

Figure 12:
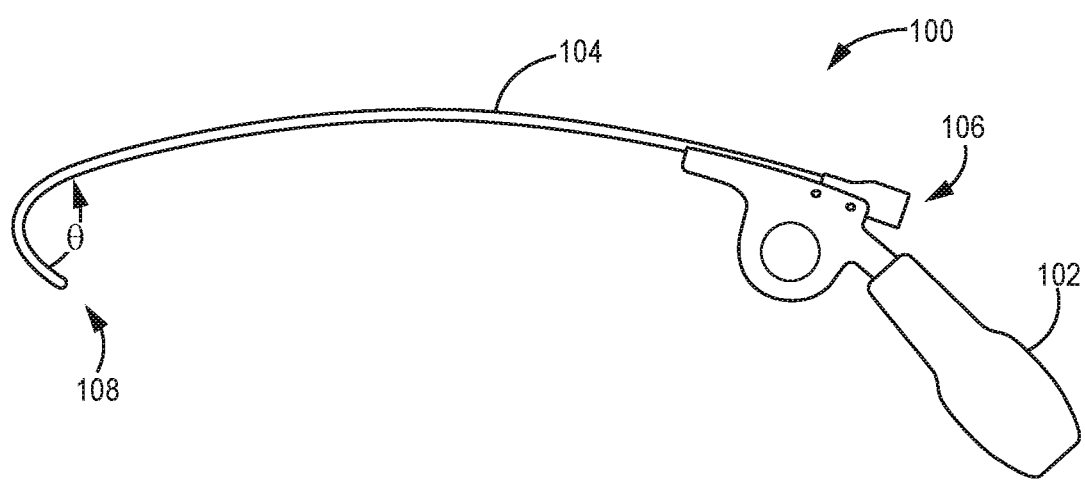
FIG. 12 is a plan view of an exemplary medical electrical lead connected through to a guide catheter
Figure 15:
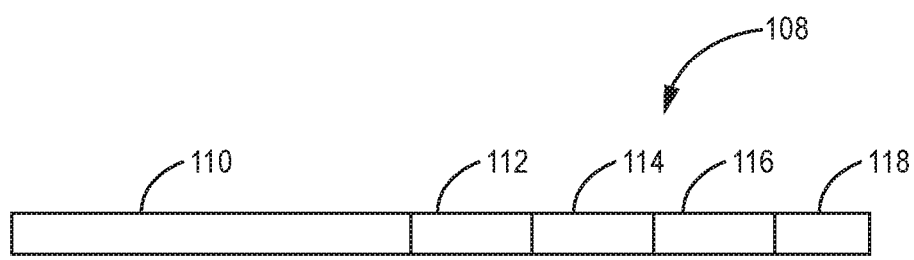
FIG. 15 is a schematic diagram depicting a catheter.

The method of placing the lead 18 begins at block 202 in which the lead 18 is loaded into a valve of the guide catheter 100, as shown in FIG. 12. At block 204, pericardial access is attained through a supxiphoidal puncture with a small needle such as a Tuohy needle ranging in size from about 22 G to about 25 G. In particular, to ensure the process is minimally invasive, a percutaneous puncture is employed with a left lateral (i.e. intercostal) thoracascope port for visualization. At block 206, a guiding catheter 100 or delivery device is introduced into the pericardial space. The outer catheter 104 is deflected by rotating the handle 102. The guiding catheter 100 includes an outer deflectable catheter 104 and an inner catheter assembly 108 that are positionable within a lumen of the outer catheter and extendible beyond a distal end of the outer catheter. The inner catheter assembly 108 includes a pre-formed inner catheter 104 (e.g. shaft configurations can be, for example, cf3 and cf4) with a soft tip. In one or more other embodiments, catheter 108 is configured to be employed as a single catheter as shown in FIG. 15 with a lumen (not shown) to receive epicardial lead 18. Catheter 108 comprises a set of segments 110-118 in which the distal tip 118 comprises softer and more flexible material (i.e. 35 durometer (D)) compared to more proximal segments 110-116. For example, one-inch segments 112, 114 and 116 comprise 72D, 63D, and 55D, respectively. Softer more flexible material is used at distal tip 118 as compared to segments 112-116. Distal tip 116 extends about one inch from segment 116. Distal tip 118 allows for easier navigation of the catheter in the patient's body. The distal tip 118 of catheter 108 can include a variety of different shapes, as is shown in FIGS. 16-18 and described in the accompanying text.

At block 208, the guiding catheter 100 (e.g. outer catheter if inner and outer catheter are used) is navigated to the optimal location such that lead 18 approaches the pericardial space of the heart after passing through the subxiphoid access. The epicardial fixation lead 18 includes a side fixation helix oriented to solely grasp the epicardial tissue but the side fixation helix 30. Epicardial lead 18 does not attach to the pericardial tissue. Lead 18 is passed posterior when positioning the defibrillation electrode such that the placing of the defibrillation electrode is placed high on the heart at the base of the atrium. The fixation helix 30 is screwed into the ventricular tissue just below the AV groove. The ring electrode is positioned adjacent the pacing location. Typically, pacing occurs from the ring electrode 29 to the defibrillation coil 27 using a bipolar construction for the lead 18.

At block 210, medical personnel such as a physician determines that the target site has been reached with the assistance of visual images and/or results obtained through testing. For example, the side helix 30 is positioned over ventricular tissue near the AV groove. At block 212, the process of pushing the lead 18 out of catheter 100 begins by causing the inner catheter assembly 108 to gradually exit the distal end of the outer catheter 104. While the inner catheter assembly 108 begins to move out of the distal end of the shaft of the outer catheter assembly. In particular, the epicardial lead 18 (e.g. 4.1 French) with a long tip electrode used for defibrillation or in conjunction with a ring electrode for pacing, has moved in a distal direction out of the guiding catheter 100 toward the target location. The lead is attached to the epicardial tissue when the inner catheter assembly is extended beyond the distal end of the outer catheter. The lead is fixated to the target location by turning the lead in a clockwise direction to allow the side helical tip to solely screw-in to the epicardial tissue. Window 32 in side helical fixation member 30 allows the physician to visualize the turns of the side helical member 30 using the fluoroscopy during the implantation procedure. For example, the physician can position the lead 18, and, when ready, watch as the helix turns using the window portion 32 as a means to track turning of the side helical fixation member 30. Without fluoroscopy, either a videoscope is used to visualize turning of the side helix or lead body torque feedback is employed as described in U.S. patent application Ser. No. 14/696,242, entitled METHOD AND APPARATUS FOR DETERMINING SUITABILITY OF A LEAD IMPLANT LOCATION, incorporated by reference in its entirety herein.

The side helical member 30, with a substantially flat and tapered distal tip and changing diameter creates a "wedging effect" of the tissue such that the tissue has a thicker edge at a proximal end and a thinner edge at distal end of the tapered tip of side helical member 30. The diameter change associated with fixation member 30 ranges from about 1.5 mm to about 2.5 mm. Additionally, the distal tip of the side helix 30 is configured to perform a minimum of at least ¾ turns in epicardial tissue. The distal tip of the side helix 30 solely enters and attaches to epicardial tissue. The flat pitch of the distal tip reduces auto-rotation.

In contrast to the presently disclosed lead 18, the lead in Stokes et al. is unable to be fixated solely in the epicardial tissue since the Stokes et al. lead penetrates the epicardium and resides mid-myocardial for stimulation. Additionally, the Stokes et al. distal tip increases auto-rotation.

The IMD 10 is then implanted in the abdominal area while the shock vectors are positioned across the atria through the ventricles to the device. The ring electrode is positioned just below the AV groove at the epicardial surface. Lead 18 is placed on epicardial surface and paces the left ventricle at a basal location.

Once the lead 18 is placed at the desired location and the IMD 10 is implanted, any equipment not intended for long term implant, e.g. guide catheter, stylet, guidewire, etc. can be removed. For example, the guiding catheter and sheaths (e.g. outer sheaths are about 9 to 10 French) are then slit and removed. Thereafter, the IMD is placed in an appropriate location.

By employing method 200, a catheter can be used to place the epicardial lead in any location around the surface of the heart such as atrial lead deployment, left ventricular lead deployment, lead in the right atrium, lead fixed to the right ventricle, and lead fixed to a backside of the heart. It is beneficial to be able to use a single catheter for lead placement anywhere around the heart and not be limited to placement locations of the lead due to guide catheter constraints such as being unable to get behind the heart.

Epicardial lead implantation requires surgical access to allow sufficient room to position and fixate the pacing lead tip by either sutures or a right-angle helical screw component. Surgical access is more traumatic and requires longer recovery time as compared to percutaneous implant methods.

Figure 14:
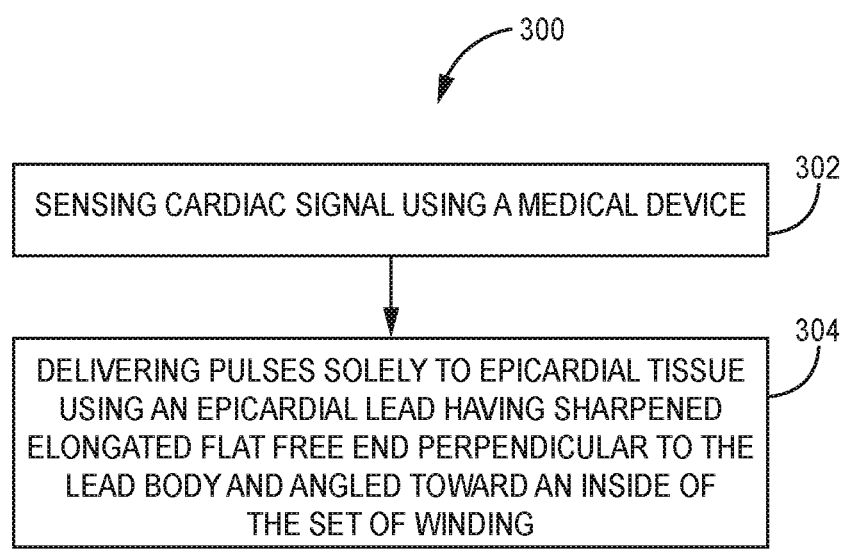
FIG. 14 is a flow diagram of a method of using an epicardial medical electrical lead.

FIG. 14 involves a method 300 of using an implantable medical device with an epicardial lead 18 extending therefrom. At block 302, a cardiac signal is sensed via a pace/sense electrode on the epicardial lead 18. At block 304, pulses are delivered to epicardial tissue using an epicardial lead 18. The epicardial lead 18 has a sharpened elongated flat free end perpendicular to the lead body and angled toward an inside of the set of winding.

FIGS. 16A-16D through FIGS. 18A-18D depict minimally invasive subxyphoid delivery tool (e.g. catheter 108) that has one of the distal tips 400-900 employed for placement of the side helix active fixation epicardial lead 18. Delivery tool distal tips 400-900 are used to place lead 18 via a single percutaneous access site. Delivery tool distal tips 400-900 gain access to the pericardial space and navigate around the heart to the desired location to place lead 18 epicardially. Each delivery tool distal tips 400-900 on the catheter ensures that the side helix active fixation mechanism 30 engages solely with epicardial tissue and not the pericardial sac, which is necessary to ensure that the therapy is directed into the epicardial tissue.

The catheter distal tip (also referred to as a protrusion or shovel) is formed or attached at the distal end of the delivery device (also referred to as a catheter and shown in FIG. 15) to slide between epicardial tissue and the pericardial sac. The distal tip is movable to cover the side helical fixation member 30 to ensure that the helical fixation member 30 is directly positioned solely into the epicardial surface and not pericardial sac. For example, when delivering the lead 18 (i.e. lead 18 protrudes away or past the distal end of the catheter) the helix 30 becomes exposed so that the physician can determine the location of helix 30 relative to the catheter 108. Once the helix 30 is exposed, the physician can either pull the lead 18 in a proximal direction or can push the catheter distally over the lead 18 in order to shield the helix 30 on lead 18. The distal tip, which serves as a shield, covers the helix 30 to ensure that the helix 30 will not attach to the pericardial sac and will only enter the epicardial tissue. When the physician is satisfied with the lead position, the catheter with the shield shown in FIGS. 16-18, will be retracted. A slitting tool is used to remove the catheter 108 from the lead 18.

Figure 16A:
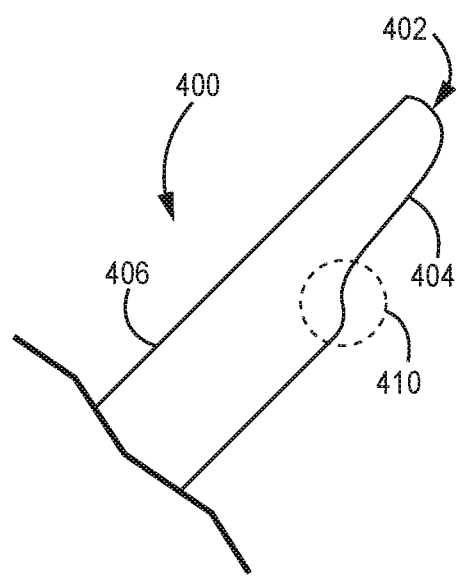
FIG. 16A is a schematic diagram depicting a side view of an embodiment of a catheter tip.
Figure 16B:
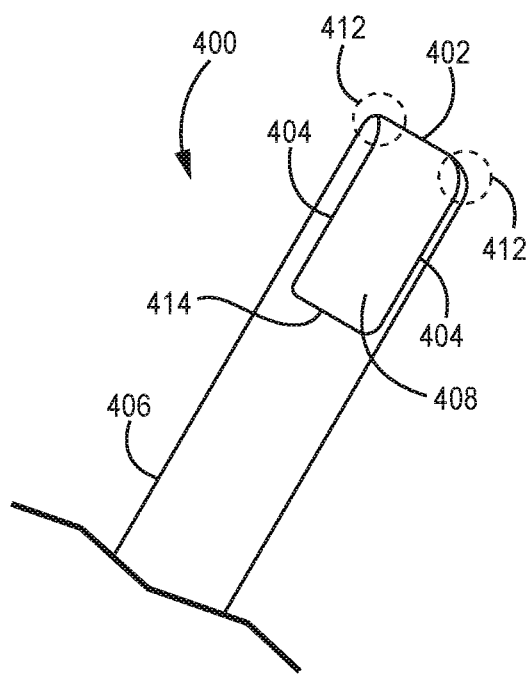
FIG. 16B is a schematic diagram depicting a view of the catheter tip of FIG. 16A in which a concave surface of the catheter tip surface is shown with a substantially open rectangular portion.
Figure 16C:
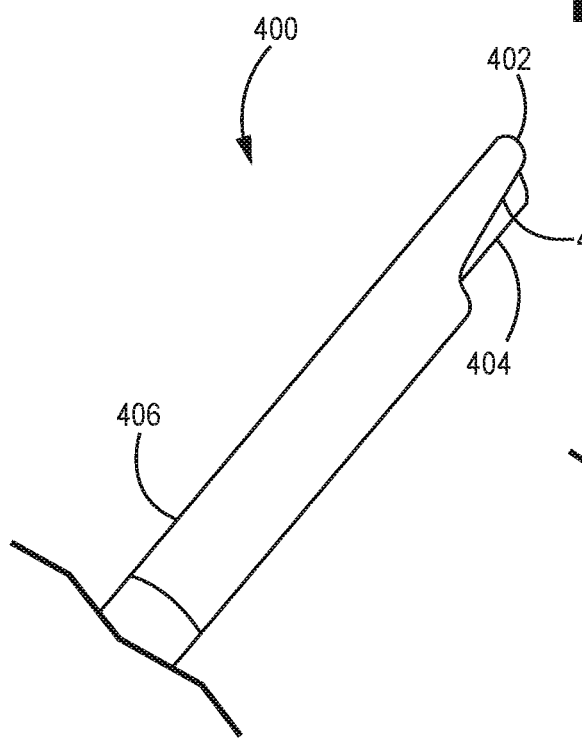
FIG. 16C is a schematic diagram depicting a side view of the catheter tip of FIG. 16A slightly rotated to show a side of the tip.
Figure 16D:
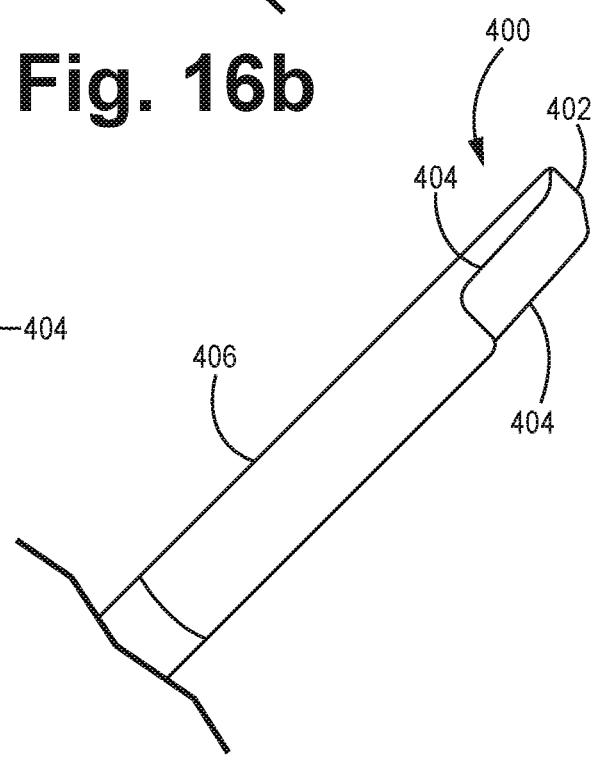
FIG. 16D is a schematic diagram depicting a side view of the catheter tip of FIG. 16C slightly rotated relative to FIG. 16C to show a side of the tip.

FIGS. 16A-16D show one embodiment of a catheter tip 400. FIG. 16A depicts a side view of catheter tip 400. FIG. 16B shows catheter tip 400, rotated 90 degrees from its position in FIG. 16A, thereby displaying a concave surface 408 with a substantially open rectangular portion formed by sides 404 and distal end 402. FIG. 16C depicts a side view of the catheter tip 400 slightly rotated from its position in FIG. 16A to show a portion of a side of the tip 400. Distal tip 400 is further rotated from FIG. 16C to its position in FIG. 16D to show a fuller portion of a side 404 of the tip 400.

The distal tip 400 is formed at a distal end of a catheter body 406 that includes a lumen to receive lead 18. Surface 408 (also referred to as a roof or shield) has a small radius of curvature so that surface 408 is slightly concave and serves to cover helix 30. Extending from surface 408 is substantially straight distal and side surfaces 402, 404. Distal and side surfaces 402, 404 have curved ends 410, 412 to reduce unnecessary trauma to the tissue. Optionally, the ends of each surface 404, 414 and 401 are smooth to further reduce tissue trauma.

Figure 17A:
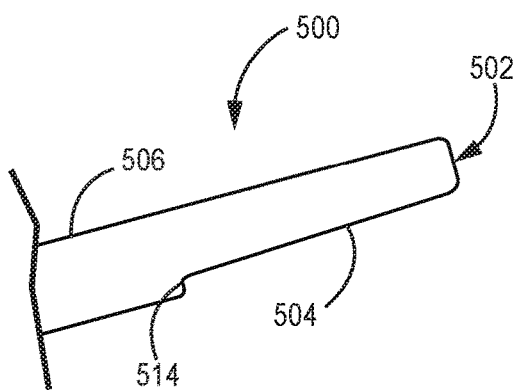
FIG. 17A is a schematic diagram depicting a side view of an embodiment of a catheter tip.
Figure 17B:
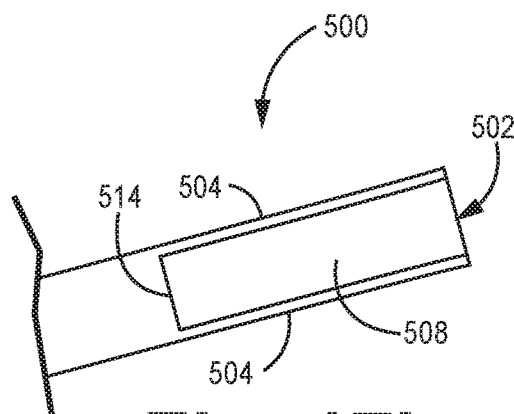
FIG. 17B is a schematic diagram depicting a view of the catheter tip of FIG. 17A in which a concave surface of the catheter tip surface is shown with a substantially open rectangular portion formed by sides and proximal and distal ends of the tip.

FIGS. 17A-17B are schematic diagrams depicting another embodiment of a catheter tip 500 in which a longer half-cut away open rectangular portion exists. The distal catheter tip 500 extends at a distal end of a catheter body 506. Tip 500 includes surface 508 that is configured with a small radius of curvature so that surface 508 is slightly concave at sides 504 that extend from surface 508. Surface 508 serves to cover helix 30. Distal end 502 is formed distally of side surfaces 502, 504. Distal and side surfaces 502, 504 are substantially straight. Distal and side surfaces 502, 504 have smooth ends 510, 512 to reduce unnecessary trauma to the tissue. Optionally, the ends of each surface 504, 514 and 501 are smooth to further reduce tissue trauma.

Figure 17C:
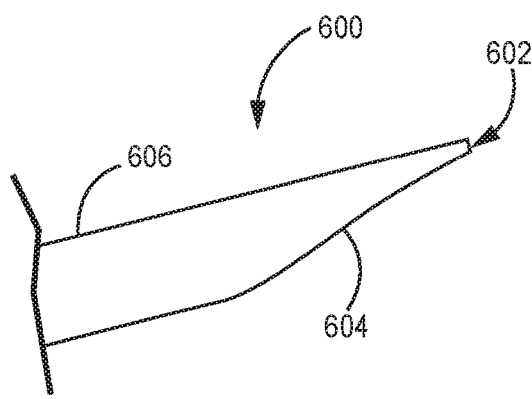
FIG. 17C is a schematic diagram depicting a side view of an embodiment of a catheter tip.
Figure 17D:
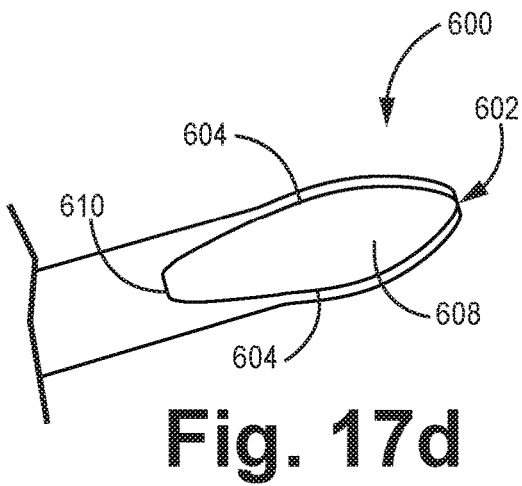
FIG. 17D is a schematic diagram depicting a view of the catheter tip of FIG. 17C in which a concave surface of the catheter tip surface is shown with a substantially open elliptical portion formed by sides and proximal and distal ends of the tip.

FIGS. 17C-17D are schematic diagrams depicting an embodiment of a sharply angled cut catheter tip 600. The distal catheter tip 600 extends from catheter body 606. Surface 608, has a small radius of curvature so that surface 608 is concave and covers helix 30. Extending from surface 608 are substantially curved side surfaces 604 with a distal end 602 that form a substantially elliptical opening. Side surface 604 is sharply tapered compared to the side surface 704 of a similarly shaped tip of FIGS. 17E-F Distal and side surfaces 602, 604 have curved ends 602, 610 to reduce unnecessary trauma to the tissue.

Figure 17E:
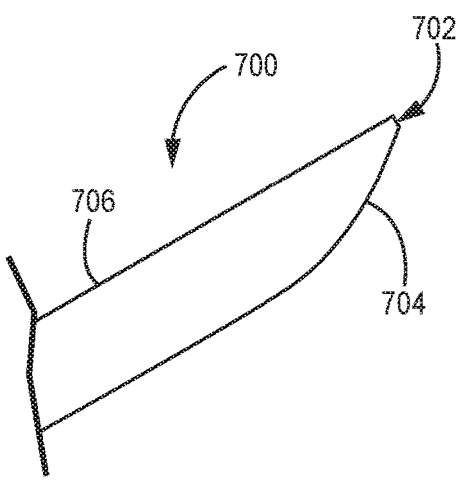
FIG. 17E is a schematic diagram depicting a side view of an embodiment of a catheter tip.
Figure 17F:
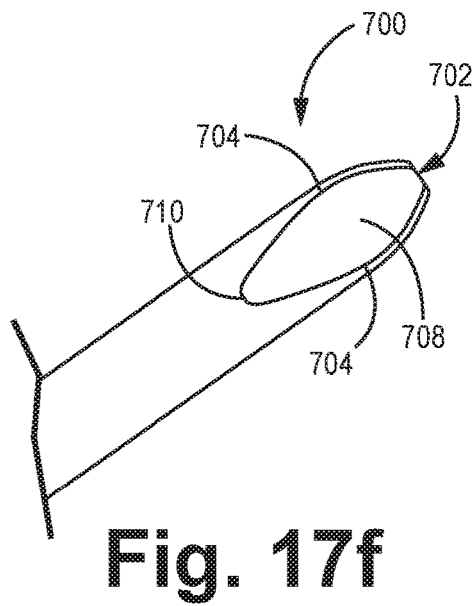
FIG. 17F is a schematic diagram depicting a view of the catheter tip of FIG. 17E in which a concave surface of the catheter tip surface is shown with a substantially open elliptical portion formed by sides and proximal and distal ends of the tip.

FIGS. 17E-17F are schematic diagrams depicting another embodiment of a catheter distal tip 700. The distal catheter tip 700 extends at a distal end of catheter body 706. Tip 700 is configured with a radius of curvature so that surface 708 is concave, with substantially curved distal and side surfaces 702, 704. Side surface 704 is less tapered or sharply cut than the side surface 604 of a similarly shaped tip. Distal and side surfaces 702, 704 have curved ends 710, 712 to reduce unnecessary trauma to the tissue and to shield helix 30.

Figure 18A:
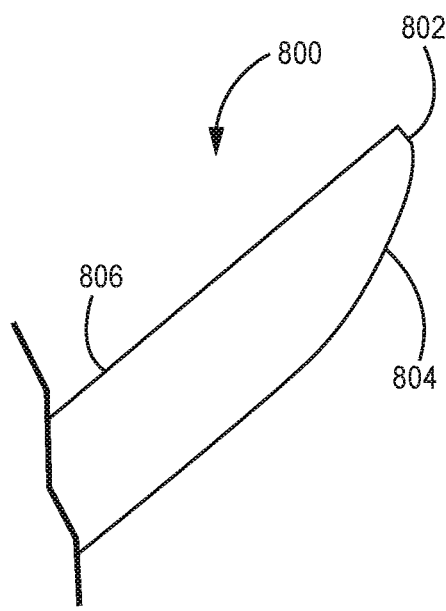
FIG. 18A is a schematic diagram depicting a side view of an embodiment of a catheter tip having an angled cut along sides of the tip.
Figure 18B:
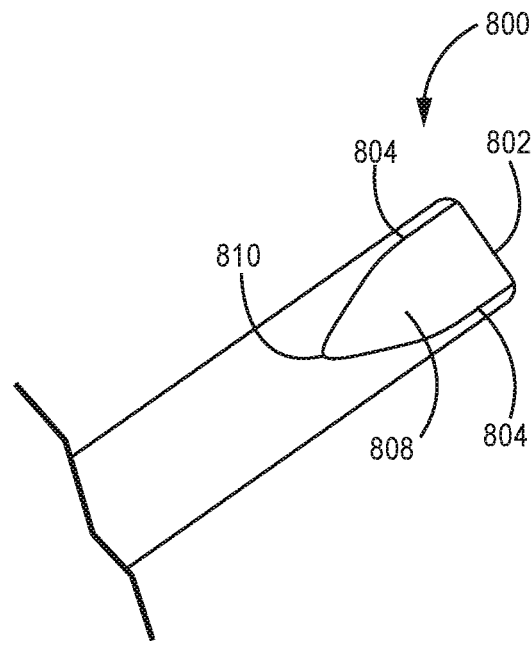
FIG. 18B is a schematic diagram depicting a view of the catheter tip of FIG. 18A in which a concave surface of the catheter tip surface is shown with a substantially open elliptical portion formed by sides and proximal and distal ends of the tip.

FIGS. 18A-18B are schematic diagrams depicting an embodiment of a catheter tip. The distal catheter tip 800 extends from catheter body 806. Surface 808 is configured with a small radius of curvature so that surface 808 is concave. Extending from surface 808 are substantially curved distal and side surfaces 802, 804 that form a substantially elliptical opening to cover helix 30. Distal and side surfaces 802, 804 that extend to curved ends 810, 812 to reduce unnecessary trauma to the tissue.

Figure 18C:
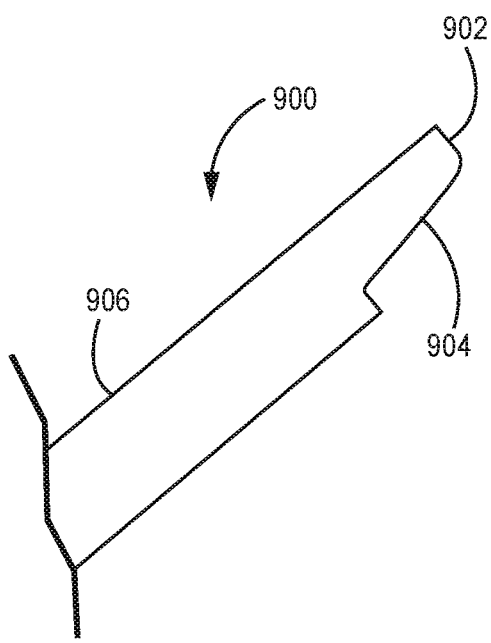
FIG. 18C is a schematic diagram depicting a side view of an embodiment of a catheter tip having sides cut away in a manner to form a substantially rectangular open portion.
Figure 18D:
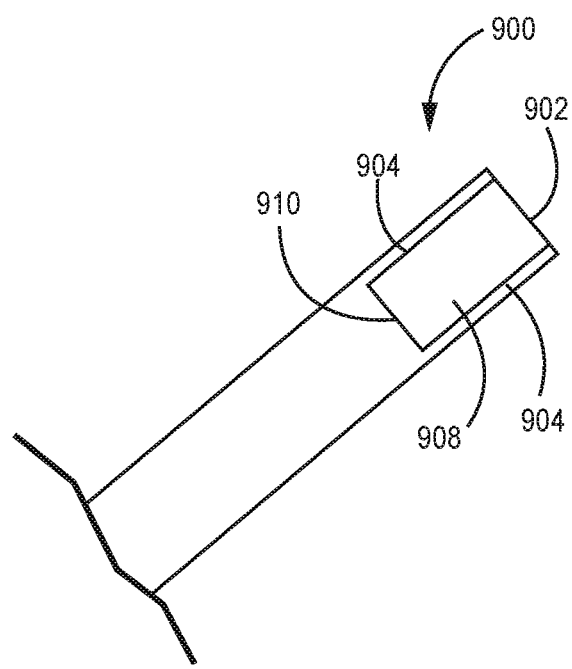
FIG. 18D is a schematic diagram depicting a view of the catheter tip of FIG. 18C in which a concave surface of the catheter tip surface is shown with a substantially open rectangular portion formed by sides and proximal and distal ends of the tip.

FIGS. 18C-18D show one embodiment of a catheter tip 900. FIG. 18A is a schematic diagram depicting a side view of an embodiment of a catheter tip while FIG. 16B shows a concave surface 908 with a substantially open rectangular portion formed by sides 904 and distal end 902. FIG. 18C depicts a side view of the catheter tip slightly rotated from FIG. 18A to show a portion of a side of the tip 900 while FIG. 18D is further rotated from FIG. 18C to show a fuller portion of a side of the tip 900.

The distal catheter tip 900 is formed at a distal end of a catheter body 906 that includes a lumen to receive lead 18. Surface 908 (also referred to as a roof) has a small radius of curvature so that surface 908 is slightly concave. Extending from surface 908 is substantially straight distal and side surfaces 902, 904. Distal and side surfaces 902, 904 have curved ends 910, 912 to reduce unnecessary trauma to the tissue. Optionally, the ends or edges of each surface 904, 914 and 901 are smooth to further reduce tissue trauma.

Distal tips 400-900 are formed by cutting away a portion of a tip or using a mold to form the tips. Tips 400-900 comprise tungsten carbide filled polyether blockamide (PE-BAX®) but can comprise other suitable materials. Catheter tip 400-900 can be made before, during or after a catheter manufacturing fusion process.

The epicardial lead 18, disclosed herein, can be used for delivery of therapy including CRT, left ventricular only pacing, defibrillation, and/or any bradycardia indication. In particular, the epicardial lead 18 utilizes a lumenless lead body design, distal high voltage coil to be positioned in the superior region of the pericardial space (i.e. transverse sinus) and fixated with a side fixation helix just proximal to the high voltage coil into the epicardial surface of the posterior LV. Either one or two ring electrodes are positioned just proximal to the side fixation helix 30 to provide ventricular pacing and sensing with additional atrial sensing in the integrated bipolar vector. Skilled artisans appreciate that while the delivery device(s) described herein have been described as delivering epicardial devices, it should be appreciated that transvenous leads can also be delivered with the delivery devices. Additionally, distal tips 400-900 for the catheter 108 can be used for a single catheter or an inner catheter to deliver a variety of leads. In addition to delivering epicardial leads, transvenous leads may also be delivered.

The following paragraphs enumerated consecutively from 1 to 24 provide for various aspects of the present disclosure. In one embodiment, a medical device comprising:

an implantable medical electrical epicardial lead that comprises:
 (a) an insulative lead body that includes a proximal end and a distal end;
 (b) at least one conductor disposed in the lead body; and
 (c) a side helical fixation member, disposed a distance from the distal end, the side helical fixation member comprising a set of windings configured to wrap around the lead body circumference, the side helical fixation member including a distal tip comprising a sharpened elongated flat free end that is perpendicular to the lead body and angled toward an inside of the set of windings.

2. The medical device of embodiment 1 wherein the fixation member includes a tapered distal tip having a substantially flat pitch.

3. The medical device of any of embodiments 1-2 wherein the flat pitch of the distal tip of the fixation member is less than 45°.

4. The medical device of any of embodiments 1-3 wherein a diameter change is associated with the tapered distal tip to create a wedging effect on tissue that causes the distal tip to solely remain in epicardial tissue.

5. The medical device of any of embodiments 1-4 wherein the diameter change associated with distal tip ranges from about 1.5 mm to about 2.5 mm.

6. The medical device of any of embodiments 1-5 wherein the flat free end is greater than 350 degrees around a circumference of the side helical fixation member.

7. The medical device of any of embodiments 1-6 wherein a clear polymer is introduced over the open portion of the side helical fixation member, the clear polymer configured to allow a physician to visualize turning of the side helical fixation member into tissue.

8. The medical device of any of embodiments 1-7 wherein a polymer is introduced over the open portion of the side helical fixation member and over a portion of the set of windings to secure the side helical fixation member to the lead body.

9. The medical device of any of embodiments 1-8 wherein the distal tip of the side helical fixation member is configured to perform a minimum of at least ¾ turn in tissue.

10. The medical device of any of embodiments 1-9 wherein the side helical fixation member disposed at a distance of about 3 cm to about 12 cm from the distal end.

11. The medical device of any of embodiments 1-10 wherein the side helical fixation mechanism has a first wind that extends a small distance D2 to the second wind.

12. The medical device of any of embodiments 1-11 wherein a steep angle exists into the first wind of the helical fixation mechanism.

13. The medical device of any of embodiments 1-12 wherein a shallow angle into tip exists in the side helical fixation mechanism.

14. A method for employing a medical device having a housing, a processor disposed within the housing, and a medical electrical epicardial lead connected to the processor through a connector module, the method comprising:

using the epicardial lead to sense a response from cardiac tissue, the lead comprising:
 (a) an insulative lead body that includes a proximal end and a distal end;
 (b) at least one conductor disposed in the lead body; and
 (c) a side helical fixation member, disposed a distance from the distal end, the side helical fixation member comprising a set of windings configured to wrap around a lead body circumference, the side helical fixation member including a distal tip comprising a sharpened elongated flat free end that is perpendicular to the lead body and angled toward an inside of the set of windings; and
delivering electrical pulses through the lead to tissue of a patient in response to sensing the response.

15. A medical device system comprising:
a delivery device having a proximal end and a distal end with an interior therebetween, the distal end having a distal tip, an opening to the interior of the delivery device at the distal end of the device, the opening and extending longitudinally proximal from the distal end of the device, the opening defined by longitudinally extending side edges and a distal edge at the distal end of the delivery device;
an implantable medical electrical epicardial lead that comprises:
 (a) an insulative lead body that includes a proximal end and a distal end;
 (b) at least one conductor disposed in the lead body; and
 (c) a side helical fixation member, disposed a distance from the distal end, the side helical fixation member comprising a set of windings configured to wrap around the lead body circumference, the side helical fixation member including a distal tip comprising a sharpened elongated flat free end that is perpendicular to the lead body and angled toward an inside of the set of windings,
 wherein the distal tip of the delivery device is movable over the side helical fixation member.

16. The medical device system of embodiment 15 wherein the distal tip of the delivery device having a concave surface with a distal edge and side edge.

17. The medical device system of any of embodiments 15-16 wherein the distal tip of the delivery device includes curved distal edge and side edges.

18. The medical device system of any of embodiments 15-17 wherein the distal tip of the delivery device includes straight distal edge and a side edges.

19. The medical device system of any of embodiments 15-18 wherein the distal tip of the delivery device includes straight distal edge and a side edges are smooth.

20. The medical device system of any of embodiments 15-19 wherein the distal tip of the delivery device includes straight distal edge and side edges without sharp edges.

21. The medical device system of any of embodiments 15-20 wherein the distal tip of the delivery device includes a rectangular opening.

22. The medical device system of any of embodiments 15-21 wherein the distal tip of the delivery device includes an elliptical opening.

23. A system for employing a medical device having a housing, a processor disposed within the housing, and a medical electrical epicardial lead connected to the processor through a connector module, the method comprising:
  processor means for using the epicardial lead to sense a response from cardiac tissue, the lead comprising:
    (a) an insulative lead body that includes a proximal end and a distal end;
    (b) at least one conductor disposed in the lead body; and
    (c) a side helical fixation member, disposed a distance from the distal end, the side helical fixation member comprising a set of windings configured to wrap around a lead body circumference, the side helical fixation member including a distal tip comprising a sharpened elongated flat free end that is perpendicular to the lead body and angled toward an inside of the set of windings; and
  delivering electrical pulses through the lead to tissue of a patient in response to sensing the response.

A kit comprising:
a delivery device having a proximal end and a distal end with an interior therebetween, the distal end having a distal tip, an opening to the interior of the delivery device at the distal end of the device, the opening and extending longitudinally proximal from the distal end of the device, the opening defined by longitudinally extending side edges and a distal edge at the distal end of the delivery device;
an implantable medical electrical epicardial lead that comprises:
  (a) an insulative lead body that includes a proximal end and a distal end;
  (b) at least one conductor disposed in the lead body; and
  (c) a side helical fixation member, disposed a distance from the distal end, the side helical fixation member comprising a set of windings configured to wrap around the lead body circumference, the side helical fixation member including a distal tip comprising a sharpened elongated flat free end that is perpendicular to the lead body and angled toward an inside of the set of windings,
    wherein the distal tip of the delivery device is movable over the side helical fixation member.

Although the present invention has been described in considerable detail with reference to certain disclosed embodiments, the disclosed embodiments are presented for purposes of illustration and not limitation and other embodiments of the invention are possible. It will be appreciated that various changes, adaptations, and modifications may be made without departing from the spirit of the invention and the scope of the appended claims.

What is claimed is:

1. A medical device system comprising:
  a delivery device having a proximal end and a distal end with an interior therebetween, the distal end having a distal tip and an opening to an interior of the delivery device, the opening extending longitudinally proximal from the distal end of the device, the opening defined by longitudinally extending side edges and a distal edge at the distal end of the delivery device;
  an implantable medical electrical epicardial lead that comprises:
    (a) an insulative lead body that includes a proximal end and a distal end;
    (b) at least one conductor disposed in the lead body; and
    (c) a side helical fixation member, disposed a distance from the distal end, the side helical fixation member comprising a set of windings configured to wrap around the lead body circumference, the side helical fixation member including a distal tip comprising a sharpened elongated free end and comprising a final one of the windings defining an angle of 15 degrees or less with regard to a line perpendicular to the centerline.

2. The medical device system of claim 1 wherein the distal tip of the delivery device includes a concave surface.

3. The medical device system of claim 1 wherein the distal tip of the delivery device includes a curved distal edge.

4. The medical device system of claim 1 wherein the distal tip of the delivery device includes a straight distal edge.

5. The medical device system of claim 1 wherein the distal tip of the delivery device includes a straight distal edge and smooth side edges.

6. The medical device system of claim 1 wherein the distal tip of the delivery device includes a straight distal edge and side edges without sharp edges.

7. The medical device system of claim 1 wherein the distal tip of the delivery device includes a rectangular opening.

8. The medical device system of claim 1 wherein the distal tip of the delivery device includes an elliptical opening.

9. The medical device system of claim 1 wherein the distal tip of the delivery device is movable over the side helical fixation member.

10. The kit of claim 1 wherein the distal tip of the delivery device includes a straight distal edge and side edges without sharp edges.

11. A kit comprising:
  a delivery device having a proximal end and a distal end with an interior therebetween, the distal end having a distal tip and an opening to an interior of the delivery device, the opening extending longitudinally proximal from the distal end of the device, the opening defined by longitudinally extending side edges and a distal edge at the distal end of the delivery device;
  an implantable medical electrical epicardial lead that comprises:
    (a) an insulative lead body that includes a proximal end and a distal end;
    (b) at least one conductor disposed in the lead body; and
    (c) a side helical fixation member, disposed a distance from the distal end, the side helical fixation member comprising a set of windings configured to wrap around the lead body circumference, the side helical fixation member including a distal tip comprising a sharpened elongated free end and comprising a final one of the windings defining an angle of 15 degrees or less with regard to a line perpendicular to the centerline.

12. The kit of claim 11 wherein the distal tip of the delivery device is movable over the side helical fixation member.

13. The kit of claim 11 wherein the distal tip of the delivery device includes a concave surface.

14. The kit of claim 11 wherein the distal tip of the delivery device includes a curved distal edge.

15. The kit of claim 11 wherein the distal tip of the delivery device includes a straight distal edge.

16. The kit of claim 11 wherein the distal tip of the delivery device includes a straight distal edge and smooth side edges.

17. The kit of claim 11 wherein the distal tip of the delivery device includes a rectangular opening.

18. The kit of claim 11 wherein the distal tip of the delivery device includes an elliptical opening.

\* \* \* \* \*